United States Patent
Nudler et al.

(10) Patent No.: US 10,059,944 B2
(45) Date of Patent: *Aug. 28, 2018

(54) SIRNA TARGETING HSR1

(71) Applicant: New York University, New York, NY (US)

(72) Inventors: Evgeny A. Nudler, New York, NY (US); Bibhusita Pani, New York, NY (US)

(73) Assignee: New York University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/776,469

(22) PCT Filed: Mar. 14, 2014

(86) PCT No.: PCT/US2014/029358
§ 371 (c)(1),
(2) Date: Sep. 14, 2015

(87) PCT Pub. No.: WO2014/144799
PCT Pub. Date: Sep. 18, 2014

(65) Prior Publication Data
US 2016/0122757 A1    May 5, 2016

Related U.S. Application Data

(60) Provisional application No. 61/800,192, filed on Mar. 15, 2013.

(51) Int. Cl.
C12N 15/11 (2006.01)
C12N 15/113 (2010.01)

(52) U.S. Cl.
CPC ........ *C12N 15/113* (2013.01); *C12N 2310/11* (2013.01); *C12N 2310/14* (2013.01); *C12N 2310/3231* (2013.01)

(58) Field of Classification Search
None
See application file for complete search history.

(56) References Cited

U.S. PATENT DOCUMENTS

| | | |
|---|---|---|
| 7,919,603 B2 | 4/2011 | Nudler et al. |
| 8,067,558 B2 | 11/2011 | Nudler et al. |
| 8,344,128 B2 | 1/2013 | Natt et al. |
| 8,389,711 B2 | 3/2013 | Hoshi et al. |
| 8,889,850 B2 | 11/2014 | Nudler et al. |
| 2004/0255346 A1 | 12/2004 | Charng et al. |
| 2005/0245475 A1 | 11/2005 | Khvorova et al. |
| 2007/0238682 A1 | 10/2007 | Nudler et al. |
| 2009/0188009 A1 | 7/2009 | Nudler et al. |
| 2012/0142100 A1 | 6/2012 | Nudler et al. |

OTHER PUBLICATIONS

Mercer et al., Long non-coding RNAs: insights into functions, 2009, Nature Reviews Genetics, vol. 10, pp. 155-159.*
Rose et al., Funtional polarity is introduced by Dicer processing of short substrate RNAs, 2005, Nucleic Acids Research, vol. 33, pp. 4140-4156.*
Aigner et al., "Gene silencing through RNA interference (RNAi) in vivo: strategies based on the direct application of siRNAs." J Biotechnol., (Jun. 25, 2006), vol. 124:1, pp. 12-25. Epub Jan. 18, 2006.
Allen et al., "The SINE-Encoded Mouse B2 RNA Represses mRNA Transcription in Response to Heat Shock." Nature Structural & Molecular Biology, (Sep. 2004), vol. 11, No. 9, pp. 816-821.
Brands et al., "The primary structure of the alpha subunit of human elongation factor 1 structural aspects of guanine-nucleotide-binding sites." European Journal of Biochemistry, (1986), vol. 155, pp. 167-171.
Calderwood et al., "Targeting HSP7O-Induced Thermotolerance for Design of Thermal Sensitizers." International Journal of Hyperthermia, (2002), vol. 18, No. 6, pp. 597-608.
Ciocca et al., "Response of Human Breast Cancer Cells to Heat Shock and Chemotherapeutic Drugs." Cancer Research, (1992), vol. 52, pp. 3648-3654.
Copley et al., "Genome and protein evolution in eukaryotes." Current Opinion in Chemical Biology, (Feb. 1, 2002), vol. 6:1, pp. 39-45.
Espinoza et al., "B2 RNA Binds Directly to RNA Polymerase II to Repress Transcript Synthesis." Nature Structural & Molecular Biology, (Sep. 2004), vol. 11, No. 9, pp. 822-829.
Guo et al., "Evidence for a Mechanism of Repression of Heat Shock Factor 1 Transcriptional Activity by a Multichaperone Complex." The Journal of Biological Chemistry, (Dec. 7, 2001), vol. 276, No. 49, pp. 45791-45799.
Hargitai et al., "Bimoclomol, a Heat Shock Protein Co-Inducer, Acts by the Prolonged Activation of Heat Shock Factor-1." Biochemical and Biophysical Research Communications, (2003), vol. 307, pp. 689-695.
Ianaro et al., "Anti-Inflammatory Activity of 15-Deoxy-Δ2,14-PGJ2 and 2-Cyclopenten-1-one: Role of the Heat Shock Response." Molecular Pharmacology, (2003), vol. 64, No. 1, pp. 85-93.
Jolly et al., "Role of the Heat Shock Response and Molecular Chaperones in Oncogenesis and Cell Death." Journal of the National Cancer Institute, (Oct. 4, 2000), vol. 92, No. 19, pp. 1564-1572.
Kim et al., "Heat-shock proteins: new keys to the development of cytoprotective therapies." Expert Opin. Ther. Targets, (2006), vol. 10, pp. 759-769.

(Continued)

*Primary Examiner* — Dana H Shin
(74) *Attorney, Agent, or Firm* — Troutman Sanders LLP

(57) ABSTRACT

The invention provides siRNA molecules, combinations of such siRNA molecules, and locked nucleic acid (LNA) antisense oligonucleotides, which target Heat Shock RNA (HSR1) and effectively inhibit stress response in a cell, as well as the use of such siRNA molecules and LNA antisense oligonucleotides for inhibiting inflammatory reactions, inhibiting HIV transcription, and treatment of various diseases, including autoimmune diseases and cancer.

10 Claims, 6 Drawing Sheets

Specification includes a Sequence Listing.

(56) References Cited

OTHER PUBLICATIONS

Kugel et al., "Beating the Heat: A Translation Factor and an RNA Mobilize the Heat Shock Transcription Factor HSF-1." Molecular Cell, (Apr. 21, 2006), vol. 22, pp. 153-154.
Margulis, "Biodiversity: molecular biological domains, symbiosis and kingdom origins." Biosystems, (1992), vol. 27:1, pp. 39-51.
Morimoto, "Regulation of the Heat Shock Transcriptional Response: Cross Talk Between a Family of Heat Shock Factors, Molecular Chaperones, and Negative Regulators." Genes & Development, (1998), vol. 12, pp. 3788-3796.
Nguyen et al., "7SK Small Nuclear RNA Binds to and Inhibits the Activity of CDK9/Cyclin T Complexes." Nature, (Nov. 15, 2001), vol. 414, pp. 322-325.
Nudler et al., "Methods of Walking with the RNA Polymerase." Methods in Enzymology, vol. 371, (2003), pp. 160-169.
Oshima et al., "Cloning, sequencing, and expression of cDNA for human b-glucuronidase." PNAS, (1987), vol. 84, pp. 685-689.
Powers et al., "Inhibitors of the Heat Shock Response: Biology and Pharmacology." FEBS Letters, (2007), vol. 581, pp. 3758-3769.
Prasnath et al., "Eukaryotic regulatory RNAs: an answer to the 'genome complexity' conundrum." Genes Dev., (2007), vol. 21, pp. 11-42.
Rabindran et al., "Molecular cloning and expression of a human heat shock factor,HSF1." PNAS, (1991), vol. 88, pp. 6906-6910.
Reeder et al., "Beyond Mfold: recent advances in RNA bioinformatics." J Biotechnol., (2006), vol. 124(1), pp. 41-55. Epub Mar. 10, 2006.
Samarsky et al., "Expressing active ribozymes in cells." Curr Issues Mol Biol., (Jul. 2000), vol. 2:3, pp. 87-93.
Sandy, et al., "Mammalian RNAi: a practical guide." BioTechniques; Massachusetts Institute of Technology, Cambridge, MA, US, (2005); vol. 39, No. 2, pp. 215-224.
Shamovsky et al., "Novel regulatory factors of HSF-1 activation: facts and perspectives regarding their involvement in the age-associated attenuation of the heat shock response", Mechanisms of Ageing and Development, (2004), vol. 125, pp. 767-775.
Shamovsky et al., "RNA-Mediated Response to Heat Shock in Mammalian Cells." Nature, (Mar. 23, 2006), vol. 440, pp. 556-560.
Shamovsky et al., "Isolation and characterization of the Heat Schock RNA 1, Methods in Molecular Biology." A. Serganov (ed), Humana Press, (2009), vol. 540, Chapter 19, pp. 265-279.
Sigmund, "Viewpoint: Are studies in genetically altered mice out of control?" Atherosclerosis, Thrombosis, Vascular Biology, (2000), vol. 20, pp. 1425-1429.
Voellmy, "On Mechanisms That Control Heat Shock Transcription Factor Activity in Metazoan Cells." Cell Stress & Chaperones, (2004), vol. 9, No. 2, pp. 122-133.
Westerheide et al., "Heat Shock Response Modulators as Therapeutic Tools for Diseases of Protein Conformation." The Journal of Biological Chemistry, (Sep. 30, 2005), vol. 280, No. 39, pp. 33097-33100.
Yang et al., "The 7SK Small Nuclear RNA Inhibits the CDK9/Cyclin T1 Kinase to Control Transcription." Nature, (Nov. 15, 2001), vol. 414, pp. 317-322.
Zou et al., "Heat Shock Transcription Factor 1 Protects Cardiomyocytes From Ischemia/Reperfusion Injury." Circulation, (Dec. 16, 2003), pp. 3024-3030.
International Search Report for International Application No. PCT/US2006/062279, dated Jul. 11, 2008.
International Preliminary Report on Patentability for International Application No. PCT/US2006/062279, dated Aug. 26, 2008.
International Search Report for International Application No. PCT/US2008/082078, dated Mar. 16, 2009.
International Preliminary Report on Patentability for International Application No. PCT/US2008/082078, dated May 4, 2010.
International Search Report and Written Opinion Issued in International Application No. PCT/US2014/029358, dated Nov. 13, 2014.
International Preliminary Report on Patentability Issued in International Application No. PCT/US2014/029358, dated Oct. 20, 2015.
Written Opinion Issued in International Application No. PCT/US2006/062279, dated Jun. 18, 2008.
Watanabe; Toshiaki et al., "Endogenous siRNAs from naturally formed dsRNAs regulate transcripts in mouse oocytes", Nature (2008), vol. 453, pp. 539-544, doi:10.1038/nature06908.

\* cited by examiner

SEQUENCE LISTING

<160> NUMBER OF SEQ ID NOS: 21

<210> SEQ ID NO 1
<211> LENGTH: 27
<212> TYPE: RNA
<213> ORGANISM: Artificial Sequence
<220> FEATURE:
<223> OTHER INFORMATION: siRNA

<400> SEQUENCE: 1
aucuccuaaa gaaugauugu aguccuc                                          27

<210> SEQ ID NO 2
<211> LENGTH: 25
<212> TYPE: DNA
<213> ORGANISM: Artificial Sequence
<220> FEATURE:
<223> OTHER INFORMATION: siRNA

<400> SEQUENCE: 2
ggacuacaau cauucuuuag gagat                                            25

<210> SEQ ID NO 3
<211> LENGTH: 27
<212> TYPE: RNA
<213> ORGANISM: Artificial Sequence
<220> FEATURE:
<223> OTHER INFORMATION: siRNA

<400> SEQUENCE: 3
uggcaauugc aaugcagaua gcaagcc                                          27

<210> SEQ ID NO 4
<211> LENGTH: 25
<212> TYPE: RNA
<213> ORGANISM: Artificial Sequence
<220> FEATURE:
<223> OTHER INFORMATION: siRNA

<400> SEQUENCE: 4
cuugcuaucu gcauugcaau ugcca                                            25

<210> SEQ ID NO 5
<211> LENGTH: 562
<212> TYPE: DNA
<213> ORGANISM: Homo sapiens

<400> SEQUENCE: 5

```
aaaattcgga acgccctgt ggggaggcac gatgctgcct taactctccg ggtgatttca    60
tcttcagcgc cgagtgcgga tgcacctcgt tgaagtgctc gaaggcggcg gccatctgca   120
gcactccttc ggcctgggcc gtgtcatagt gtgttgcatc gaccggttga atccgccgcc   180
ataagcagac gttggagtgg tgtgaggact acaatcattc tttaggagat ggcattcctc   240
cttaaaccgc ctcactaagt gacgctaatg atgcctacat tgccccggag actgggctgt   300
gtaggtgcgt tcgcctccag ctttcatcgt ccgggttcat gatctaactc gttgtacaga   360
tgaagccacg tttccacctc catgaccagc ttgctgcgct gacctatcta ggtcgctggc   420
ttgctatctg cattgcaatt gccatgctgg ttggcagtgc atccgccatc tttttgcact   480
cgatggagtg ggccacccaa acgcgggacg ccaatcattg gctgatatgg ggactcccat   540
tcgcaggctt cgatgtcgac ac                                           562
```

<210> SEQ ID NO 6
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 6

```
cgccgccata agcaga                                                   16
```

<210> SEQ ID NO 7
<211> LENGTH: 27
<212> TYPE: RNA
<213> ORGANISM: Artificial Sequence
<220> FEATURE:
<223> OTHER INFORMATION: siRNA

<400> SEQUENCE: 7

```
caacacacua ugacacggcc caggccg                                       27
```

<210> SEQ ID NO 8
<211> LENGTH: 25
<212> TYPE: DNA
<213> ORGANISM: Artificial Sequence
<220> FEATURE:
<223> OTHER INFORMATION: siRNA

<400> SEQUENCE: 8

```
gccugggccg ugucauagug ugutg                                         25
```

<210> SEQ ID NO 9
<211> LENGTH: 27
<212> TYPE: RNA
<213> ORGANISM: Artificial Sequence
<220> FEATURE:
<223> OTHER INFORMATION: siRNA

<400> SEQUENCE: 9

```
uuguaguccu cacaccacuc caacguc                                       27
```

<210> SEQ ID NO 10
<211> LENGTH: 25
<212> TYPE: RNA
<213> ORGANISM: Artificial Sequence
<220> FEATURE:
<223> OTHER INFORMATION: siRNA

```
<400> SEQUENCE: 10
cguuggagug gugugaggac uacaa                                        25

<210> SEQ ID NO 11
<211> LENGTH: 27
<212> TYPE: RNA
<213> ORGANISM: Artificial Sequence
<220> FEATURE:
<223> OTHER INFORMATION: siRNA

<400> SEQUENCE: 11
gugucaugau cuccuaaucc gauauaa                                      27

<210> SEQ ID NO 12
<211> LENGTH: 26
<212> TYPE: DNA
<213> ORGANISM: Artificial Sequence
<220> FEATURE:
<223> OTHER INFORMATION: siRNA

<400> SEQUENCE: 12
guccaaucca ggagucggua gaaata                                       26

<210> SEQ ID NO 13
<211> LENGTH: 27
<212> TYPE: RNA
<213> ORGANISM: Artificial Sequence
<220> FEATURE:
<223> OTHER INFORMATION: siRNA

<400> SEQUENCE: 13
gagaguuaag gcagcaucgu gccuccc                                      27

<210> SEQ ID NO 14
<211> LENGTH: 25
<212> TYPE: DNA
<213> ORGANISM: Artificial Sequence
<220> FEATURE:
<223> OTHER INFORMATION: siRNA

<400> SEQUENCE: 14
gaggcacgau gcugccuuaa cuctc                                        25

<210> SEQ ID NO 15
<211> LENGTH: 27
<212> TYPE: RNA
<213> ORGANISM: Artificial Sequence
<220> FEATURE:
<223> OTHER INFORMATION: siRNA

<400> SEQUENCE: 15
gccuucgagc acuucaacga ggugcau                                      27

<210> SEQ ID NO 16
<211> LENGTH: 25
<212> TYPE: RNA
<213> ORGANISM: Artificial Sequence
<220> FEATURE:
<223> OTHER INFORMATION: siRNA

<400> SEQUENCE: 16
gcaccucguu gaagugcucg aaggc                                        25

<210> SEQ ID NO 17
<211> LENGTH: 27
```

```
<212> TYPE: RNA
<213> ORGANISM: Artificial Sequence
<220> FEATURE:
<223> OTHER INFORMATION: siRNA

<400> SEQUENCE: 17
cacaccacuc caacgucugc uuauggc                                           27

<210> SEQ ID NO 18
<211> LENGTH: 25
<212> TYPE: DNA
<213> ORGANISM: Artificial Sequence
<220> FEATURE:
<223> OTHER INFORMATION: siRNA

<400> SEQUENCE: 18
cauaagcaga cguuggagug gugtg                                             25

<210> SEQ ID NO 19
<211> LENGTH: 27
<212> TYPE: RNA
<213> ORGANISM: Artificial Sequence
<220> FEATURE:
<223> OTHER INFORMATION: siRNA

<400> SEQUENCE: 19
cggucgaugc aacacacuau gacacgg                                           27

<210> SEQ ID NO 20
<211> LENGTH: 25
<212> TYPE: RNA
<213> ORGANISM: Artificial Sequence
<220> FEATURE:
<223> OTHER INFORMATION: siRNA

<400> SEQUENCE: 20
gugucauagu guguugcauc gaccg                                             25

<210> SEQ ID NO 21
<211> LENGTH: 594
<212> TYPE: DNA
<213> ORGANISM: Homo sapiens

<400> SEQUENCE: 21
ccgtccaatt gaggtccgaa ccggtttaca caaaaattcg gaacgcccct gtggggaggc       60
acgatgctgc cttaactctc cgggtgattt catcttcagc gccgagtgcg gatgcacctc      120
gttgaagtgc tcgaaggcgg cggccatctg cagcactcct tcggcctggg ccgtgtcata      180
gtgtgttgca tcgaccggtt gaatccgccg ccataagcag acgttggagt ggtgtgagga      240
ctacaatcat tctttaggag atggcattcc tccttaaacc gcctcactaa gtgacgctaa      300
tgatgcctac attgccccgg agactgggct gtgtaggtgc gttcgcctcc agctttcatc      360
gtccgggttc atgatctaac tcgttgtaca gatgaagcca cgtttccacc tccatgacca      420
gcttgctgcg ctgacctatc taggtcgctg gcttgctatc tgcattgcaa ttgccatgct      480
ggttggcagt gcatccgcca tcttttttgca ctcgatggag tgggccaccc aaacgcggga     540
cgccaatcat tggctgatat ggggactccc attcgcaggc ttcgatgtcg acac            594
```

SIRNA TARGETING HSR1

CROSS-REFERENCE TO RELATED APPLICATIONS

This application is the U.S National Phase of International Patent Application Ser. No. PCT/US2014/09358, Filed Mar. 14, 2014, which claims priority to U.S. Provisional Application Ser.No. 61/800,192, filed Mar. 15, 2013, both of which applications are herein incorporated by reference in their entirety.

STATEMENT REGARDING FEDERALLY SPONSORED RESEARCH OR DEVELOPMENT

This invention made with government support under grant GM069800, awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 14, 2014, is named seq243735-122_ST25.txt, and is 5,305 bytes in size.

FIELD OF THE INVENTION

The present invention provides novel siRNA molecules and LNA antisense nucleotides which target Heat Shock RNA (HSR1) and effectively inhibit stress response in a cell, and their use for treatment of various diseases.

BACKGROUND OF THE INVENTION

The heat shock (HS) response is the major cellular defense mechanism against acute exposure to environmental stresses. The hallmark of the HS response, which is conserved in all eukaryotes, is the rapid and massive induction of expression of a set of cytoprotective genes. Most of the induction occurs at the level of transcription. The master regulator, heat shock transcription factor (HSF, or HSF1 in vertebrates), is responsible for the induction of HS gene transcription in response to elevated temperature (Voellmy, EXS, 1996, 77:121-137, Morimoto et al., EXS, 1996, 77:139-163).

It has been recently disclovered that HSF activation by heat shock is mediated by a ribonucleoprotein ternary complex comprising translation elongation factor eEF1A and a Heat Shock RNA (HSR1), a highly evolutionary conserved non-coding RNA (Shamovsky et al., Nature, 2006, 440:556-560). Among the two HSF-associated factors, HSR1 serves as a cellular thermosensor that determines the temperature threshold for the heat shock response. HSR1 and eEF1A are both required for activation of HSF and constitute a minimal functional HSR1 activating complex.

Under normal conditions HSF is present in the cell as an inactive monomer. During HS, HSF trimerizes and binds to a consensus sequence in the promoter of HS genes, stimulating their transcription by up to 200-fold. Most of these genes encode heat shock proteins (HSPs), a large family of molecular chaperones, which includes several functional and molecular weight sub-families. HSPs are essential for cell survival under normal conditions and are critical for cell survival during stress (see, e.g., Ellis, Trends Biochem Sci., 2000, 25: 210-212; Forreiter and Nover, J. Biosci., 1998, 23: 287-302; Hartl and Hayer-Hartl, Science, 2002, 295: 1852-1858; Haslbeck, Cell Mol. Life Sci., 2002, 59: 1649-1657; Young et al, Trends Biochem. Sci., 2003, 28: 541-547; Soll and Schleiff, Nature Rev. Mol. Cell. Biol., 2004, 5: 198-208). HSPs are considered a part of a protective mechanism against certain pathological conditions, including ischemic damage, neurodegenerative diseases, ageing, infection, and inflammation (Klettner, Drug News Perspect. 2004; 17:299-306; Hargitai et al., Biochem. Biophys. Res. Commun. 2003; 307:689-695; Yenari et al., Ann. Neurol. 1998; 44:584-591; Suzuki et al., J. Mol. Cell. Cardiol. 1998; 6:1129-1136; Warrik et al., Nat. Genet. 1999; 23:425-428; Pockley, Circulation 2002; 105:1012-1017; Hsu et al., Science 2003; 300:1142-5; Morley and Morimoto, Mol. Biol. Cell 2004; 15:657-64; Westerheide and Morimoto, J. Biol. Chem. 2005, 280:33097-100; Batulan et al., J. Neuosci. 2003; 23:5789-5798; Guzhova et al., Brain Res. 2001; 914:66-73; Wyttenbach et al., Human Mol. Gen. 2002; 11:1137-51; Warrick et al., Nat. Genet. 1999; 23:425-8; Krobitsch and Lindquist, Proc. Natl. Acad. Sci. USA 2000; 97:1589-94).

In the case of inflammation, a protective role of HSPs has been shown in a variety of experimental models (Jattela et al., EMBO J. 1992; 11:3507-3512; Morris et al., Int. Biochem. Cell Biol. 1995; 27:109-122; Ianaro et al., FEBS Lett. 2001; 499:239-244; Van Molle et al., Immunity 2002; 16:685-695; Plumier et al., J. Clin. Invest. 1995; 95:1854-1860; Marber et al., ibid., pp. 1446-1456; Radford et al., Proc. Natl. Acad. Sci. USA, 1996; 93:2339-2342). For example, Ianaro et al. (Mol. Pharmacol. 2003; 64:85-93) have recently demonstrated that HSF1-induced HSP72 expression in the inflamed tissues and activation of the heat shock response is closely associated with the remission of the inflammatory reaction. It follows, that HSP genes may function as anti-inflammatory or "therapeutic" genes, and their selective in vivo transactivation may lead to remission of the inflammatory reaction (Ianaro et al., FEBS Lett. 2001; 499:239-244 and Ianaro et al., FEBS Lett. 2001; 508:61-66).

Heat shock is also a known transcriptional activator of human immunodeficiency virus type 1 (HIV) long terminal repeat (LTR). However, HIV LTR suppression can occur under hyperthermic conditions (Gerner et al., Int. J. Hyperthermia 2000; 16:171-181). Indeed, the inhibition of HIV transcription has been reported after whole-body hyperthermia at 42° C. in persons with AIDS (Steinhart et al., J. AIDS Hum. Retrovirol. 1996; 11:271-281). Recently demonstrated ability of a mutant transcriptionally active HSF1 (lacking C-terminal residues 203-315) to suppress HIV promoter activity further suggests that HSF1 could serve as a tool for the treatment of AIDS (Ignatenko and Gerner, Exp. Cell Res. 2003; 288:1-8; see also Brenner and Wainberg, Expert Opin. Biol. Ther. 2001; 1:67-77). Since HSR1 is essential for HSF1 activation, the constitutively active form of HSR1 can mimic hyperthermia and inhibit HIV transcription.

Due to interaction of HSPs with numerous regulatory proteins (e.g., NF-κB, p53, v-Src, Raf1, Akt, steroid hormone receptors) and pathways (e.g., inhibition of c-Jun NH2-terminal kinase (JNK) activation, prevention of cytochrome c release, regulation of the apoptosome, prevention of lysosomal membrane permeabilization, prevention of caspase activation) involved in the control of cell growth, the increased production of HSPs has potent anti-apoptotic effect (Bold, et al., Surgical Oncology-Oxford 1997; 6:133-142; Jaattela, et al., Exp. Cell Res. 1999; 248:30-43; Nylandsted, et al., Ann. N. Y. Acad. Sci. 2000; 926:122-125; Pratt and Toft, Exp. Biol. Med. (Maywood) 2003; 228:111-33; Mosser and Morimoto, Oncogene 2004;

23:2907-18). Anti-apoptotic and cytoprotective activities of HSPs directly implicate them in oncogenesis (Jolly and Morimoto, J. Natl. Cancer Inst. 2000; 92:1564-72; Westerheide and Morimoto, J. Biol. Chem. 2005, 280:33097-100). Many cancer cells display deregulated expression of HSPs, whose elevated levels contribute to the resistance of cancerous cells to chemo- and radiotherapy (Ciocca and Calderwood, Cell Stress Chaperones, 2005, 10:86-103; Calderwood et al., Trends Biochem Sci., 2006, 31:164-172). Different subfamilies of HSPs including HSP70, HSP90, and HSP27 were found to be expressed at abnormal levels in various human tumors (Cardoso, et al., Ann. Oncol. 2001; 12:615-620; Kiang, et al., Mol. Cell Biochem. 2000; 204: 169-178). In some cases, HSPs are expressed at cell surface in tumors, most probably serving as antigen presenting molecules in this case (Conroy, et al., Eur. J. Cancer 1998; 34:942-943). Both HSP70 and HSP90 were demonstrated to mediate cytoplasmic sequestration of p53 in cancer cells (Elledge, et al., Cancer Res. 1994; 54:3752-3757). Inactivation of wild-type p53 function has been observed in variety of cancer cells and is in fact one of the most common hallmarks in human cancer (Malkin, et al., J. Neurooncol. 2001; 51:231-243). Other studies have demonstrated that HSP70 has a potent general antiapoptotic effect protecting cells from heat shock, tumor necrosis factor, serum starvation, oxidative stress, chemotherapeutic agents (e.g., gemcitabine, torootecan, actinomycin-D, campothecin, and etoposide), and radiation (Jaattela, et al., EMBO J. 1992; 11:3507-3512; Jaattela, et al., J. Exp. Med. 1993; 177:231-236; Simon, et al., J. Clin. Invest 1995; 95:926-933; Karlseder, et al., Biochem. Biophys. Res. Commun. 1996; 220:153-159; Samali and Cotter, Exp. Cell Res. 1996; 223:163-170; Sliutz et al., Br. J. Cancer 1996; 74:172-177). At the same time, HSP70 is abundantly expressed in human malignant tumors of various origins, not only enhancing spontaneous growth of tumors, but also rendering them resistant to host defense mechanisms and therapeutic treatment (Ciocca, et al., Cancer Res. 1992; 52:3648-3654). Therefore, finding a way to suppress HSP overproduction in cancerous cells will be invaluable for increasing the efficacy of the existing anti-cancer therapeutic approaches.

SUMMARY OF THE INVENTION

As follows from the Background Section, there is a clear need in the art to develop novel therapeutically effective regulators of heat shock (HS) response in cells and tissues. The present invention satisfies this and other needs by providing siRNA molecules targeting human HSR1 (SEQ ID NO: 5) nucleotides 26-48, 204-230 and 418-444 (which correspond to human HSR1 (SEQ ID NO: 21) nucleotides 56-78, 238-260 and 452-474, respectively) and antisense oligonucleotides composed of locked nucleic acid (LNA) targeting human HSR1 (SEQ ID NO: 5) nucleotides 174-189 (correspond to human HSR1 (SEQ ID NO: 21) nucleotides 206-221) (or targeting corresponding nucleotides in HSR1 orthologs in other species), wherein said siRNA molecules and LNA antisense oligonucleotides are capable of inhibiting a stress response in a cell. In one preferred embodiment, the siRNA molecules are a combination of two or more siRNA molecules selected from the group consisting of siHSR1-1, HSR1-2 and siHSR1-4, which siRNA molecules have the following sequences:

```
siHSR1-1 (duplex sequence; targeting human HSR1
(SEQ ID NO: 5) nucleotides 204-230 or (SEQ ID
NO: 21) nucleotides 238-260)
                                         (SEQ ID NO: 1)
5'-rArUrCrUrCrCrUrArArArGrArArUrGrAr UrUrGrUrArGrUrCrCrUrC-3'

(SEQ ID NO: 2)
5'-rGrGrArCrUrArCrArArUrCrArUrUrCrUr

UrUrArGrGrArGAT-3' siHSR1-2 (duplex sequence; targeting human HSR1
(SEQ ID NO: 5) nucleotides 418-444 or (SEQ ID
NO: 21) nucleotides 452-474)
                                         (SEQ ID NO: 3)
5'-rUrGrGrCrArArUrUrGrCrArArUrGrCrAr GrArUrArGrCrArArGrCrC-3'

(SEQ ID NO: 4)
5'-rCrUrUrGrCrUrArUrCrUrGrCrArUrUrGr

CrArArUrUrGrCCA-3' siHSR1-4 (duplex sequence; targeting human HSR1
(SEQ ID NO: 5) nucleotides 26-48 or (SEQ ID
NO: 21) nucleotides 56-78)
                                         (SEQ ID NO: 13)
5'-rGrArGrArGrUrUrArArGrGrCrArGrCrAr UrCrGrUrGrCrCrUrCrCrC-3'

(SEQ ID NO: 14)
5'-rGrArGrGrCrArCrGrArUrGrCrUrGrCrCr

UrUrArArCrUrCTC-3'
```

In one preferred embodiment, the siRNA molecules are a combination of siHSR1-2 and siHSR1-4. In another preferred embodiment, the siRNA molecules are a combination of siHSR1-1 and siHSR1-4. In yet another preferred embodiment, the siRNA molecules are a combination of siHSR1-1 and siHSR1-2.

In one preferred embodiment, the antisense LNA oligonucleotide is LNA HSR1-3/4, which has the following sequence:

```
LNA HSR1-3/4 (targeting human HSR1 (SEQ ID
NO: 5) nucleotides 174-189 or (SEQ ID NO:
21) nucleotides 206-221)
                                         (SEQ ID NO: 6)
5'-CGCCGCCATAAGCAGA-3'
```

In one embodiment, the invention provides an siRNA molecule targeting nucleotides 204-230 of human HSR1 (SEQ ID NO: 5) (correspond to nucleotides 238-260 of human HSR1 (SEQ ID NO: 21)), wherein said siRNA molecule is capable of inhibiting a stress response in a cell. In one specific embodiment, such siRNA molecule comprises the sequence AUCUCCUAAAGAAUGAUUGUA-GUCCUC (SEQ ID NO: 1). In one specific embodiment, such siRNA molecule comprises the sequence GGACUA-CAAUCAUUCUUUAGGAGAT (SEQ ID NO: 2).

In one embodiment, the invention provides siRNA molecule siHSR1-1 which has the following duplex sequence:

```
                                         (SEQ ID NO: 1)
5'-rArUrCrUrCrCrUrArArArGrArArUrGrArUrUrGrUr

ArGrUrCrCrUrC-3'
```

-continued

```
                                              (SEQ ID NO: 2)
5'-rGrGrArCrUrArCrArArUrCrArUrUrCrUrUrUrArGr

GrArGAT-3'
```

In one embodiment, the invention provides an siRNA molecule targeting nucleotides 418-444 of human HSR1 (SEQ ID NO: 5) (correspond to nucleotides 452-474 of human HSR1 (SEQ ID NO: 21)), wherein said siRNA molecule is capable of inhibiting a stress response in a cell. In one specific embodiment, such siRNA molecule comprises the sequence UGGCAAUUGCAAUGCAGAUAG-CAAGCC (SEQ ID NO: 3). In one specific embodiment, such siRNA molecule comprises the sequence CUUGC-UAUCUGCAUUGCAAUUGCCA (SEQ ID NO: 4).

In one embodiment, the invention provides siRNA molecule siHSR1-2 which has the following duplex sequence:

```
                                              (SEQ ID NO: 3)
5'-rUrGrGrCrArArUrUrGrCrArArUrGrCrArGrArUrAr

GrCrArArGrCrC-3'

(SEQ ID NO: 4)
5'-rCrUrUrGrCrUrArUrCrUrGrCrArUrUrGrCrArArUr

UrGrCCA-3'
```

In one embodiment, the invention provides an siRNA molecule targeting nucleotides 26-48 of human HSR1 (SEQ ID NO: 5) (correspond to nucleotides 56-78 of human HSR1 (SEQ ID NO: 21)), wherein said siRNA molecule is capable of inhibiting a stress response in a cell. In one specific embodiment, such siRNA molecule comprises the sequence GAGAGUUAAGGCAGCAUCGUGCCUCCC (SEQ ID NO: 13). In one specific embodiment, such siRNA molecule comprises the sequence GAGGCACGAUGCUGC-CUUAACUCUC (SEQ ID NO: 14).

In one embodiment, the invention provides siRNA molecule siHSR1-4 which has the following duplex sequence:

```
                                             (SEQ ID NO: 13)
5'-rGrArGrArGrUrUrArArGrGrCrArGrCrArUrCrGrUr

GrCrCrUrCrCrC-3'

(SEQ ID NO: 14)
5'-rGrArGrGrCrArCrGrArUrGrCrUrGrCrCrUrUrArAr

CrUrCTC-3'
```

In one embodiment, the invention provides an siRNA molecule or a combination of two or more siRNA molecules targeting two or more regions of human HSR1 (SEQ ID NO: 5) selected from the group consisting of nucleotides 26-48, nucleotides 204-230 and nucleotides 418-444 (which correspond to human HSR1 (SEQ ID NO: 21) nucleotides 56-78, 238-260 and 452-474, respectively), wherein said one or more siRNA molecule(s) is capable of inhibiting a stress response in a cell.

The siRNA molecules of the invention can include one or more modifications (e.g., to the base moiety, sugar moiety, phosphate moiety, phosphate-sugar backbone, or a combination thereof).

In one embodiment, the invention provides an antisense oligonucleotide composed of locked nucleic acid (LNA), wherein said LNA antisense oligonucleotide targets nucleotides 174-189 of human HSR1 (SEQ ID NO: 5) (correspond to nucleotides 206-221 of human HSR1 (SEQ ID NO: 21)) and is capable of inhibiting a stress response in a cell. In one specific embodiment, such LNA antisense oligonucleotide comprises the sequence CGCCGCCATAAGCAGA (SEQ ID NO: 6). In one specific embodiment, such LNA antisense oligonucleotide consists of the sequence CGCCGC-CATAAGCAGA (SEQ ID NO: 6).

In a related embodiment, the invention provides pharmaceutical compositions comprising one or more siRNA molecules or LNA antisense oligonucleotides of the invention and a pharmaceutically acceptable carrier or excepient.

In another related embodiment, the present invention provides recombinant vectors and host cells (both eukaryotic and prokaryotic) which have been genetically modified to express or overexpress the siRNA molecules of the present invention.

In conjunction with the siRNA molecules and LNA antisense oligonucleotides, the present invention also provides a method for inhibiting a stress response in a cell (e.g., a cancer cell) comprising administering the siRNA molecules (e.g., two or more siRNA molecules selected from the group consisting of siHSR1-1, siHSR1-2, and siHSR1-4) or LNA antisense oligonucleotides (e.g., LNA HSR1-3/4) to the cell. As specified herein, the inhibition of the stress response in a cell can be detectable by various methods, including without limitation (i) detecting changes in the level of HSF1-mediated transcription, (ii) detecting changes in the level of a Heat Shock Protein (HSP) or mRNA encoding such HSP, and (iii) measuring thermotolerance.

The present invention further provides novel therapeutics based on the siRNA molecules (e.g., a combination of two or more siRNA molecules selected from the group consisting of siHSR1-1, siHSR1-2, and siHSR1-4) and/or LNA antisense oligonucleotides (e.g., LNA HSR1-3/4) described herein that can be used to treat various diseases in animals, including without limitation cancer, inflammation, HIV infection, and related disorders.

In one embodiment, the invention provides novel anti-cancer agents based on the siRNA molecules and LNA antisense oligonucleotides of the invention as well as methods for using these siRNA molecules and LNA antisense oligonucleotides to treat cancer. The novel anti-cancer agents of the present invention can be used in conjunction with existing treatments to improve their effect by increasing the sensitivity of the cells to pro-apoptotic stimuli such as thermo-, chemo-, and radiotherapeutic treatments.

In one embodiment, the invention provides a method for increasing sensitivity of a cancer cell to a treatment comprising administering to the cell one or more siRNA molecules (e.g., two or more siRNA molecules selected from the group consisting of siHSR1-1, siHSR1-2, and siHSR1-4) and/or LNA antisense oligonucleotides of the invention (e.g., LNA HSR1-3/4). In a specific embodiment, the treatment can be selected from the group consisting of (without limitation) radiation treatment, chemical treatment, thermal treatment, and any combination thereof.

In another embodiment, the invention provides a method for treating a cancer in a mammal (e.g., human) comprising administering to the mammal one or more siRNA molecules (e.g., two or more siRNA molecules selected from the group consisting of siHSR1-1, siHSR1-2, and siHSR1-4) and/or LNA antisense oligonucleotides of the invention (e.g., LNA HSR1-3/4).

In yet another embodiment, the invention provides a method for improving efficiency of an anti-cancer treatment in a mammal (e.g., human) comprising administering to the mammal one or more siRNA molecules (e.g., two or more siRNA molecules selected from the group consisting of siHSR1-1, siHSR1-2, and siHSR1-4) and/or LNA antisense oligonucleotides of the invention (e.g., LNA HSR1-3/4). In a specific embodiment, the mammal is further subjected to a treatment selected (without limitation) from the group consisting of radiation therapy, chemotherapy, thermotherapy, and any combination thereof. The relative timing of siRNA administration and anti-cancer treatment would depend on the delivery mechanism for siRNA and on the type of the specific anti-cancer treatment used. Generally, cells may become more sensitive to an anti-cancer treatment as soon as one hour after siRNA or LNA antisense oligonucleotide administration.

In a further embodiment, the invention provides a method for inhibiting an inflammatory reaction in a mammal (e.g., human) comprising administering to the mammal one or more siRNA molecules (e.g., two or more siRNA molecules selected from the group consisting of siHSR1-1, siHSR1-2, and siHSR1-4) or LNA antisense oligonucleotides of the invention (e.g., LNA HSR1-3/4).

In a separate embodiment, the invention provides a method for inhibiting HIV transcription in a mammal (e.g., human) comprising administering to the mammal one or more siRNA molecules (e.g., two or more siRNA molecules selected from the group consisting of siHSR1-1, siHSR1-2, and siHSR1-4) and/or LNA antisense oligonucleotides of the invention (e.g., LNA HSR1-3/4).

DETAILED DESCRIPTION OF THE INVENTION

Figure 1A:
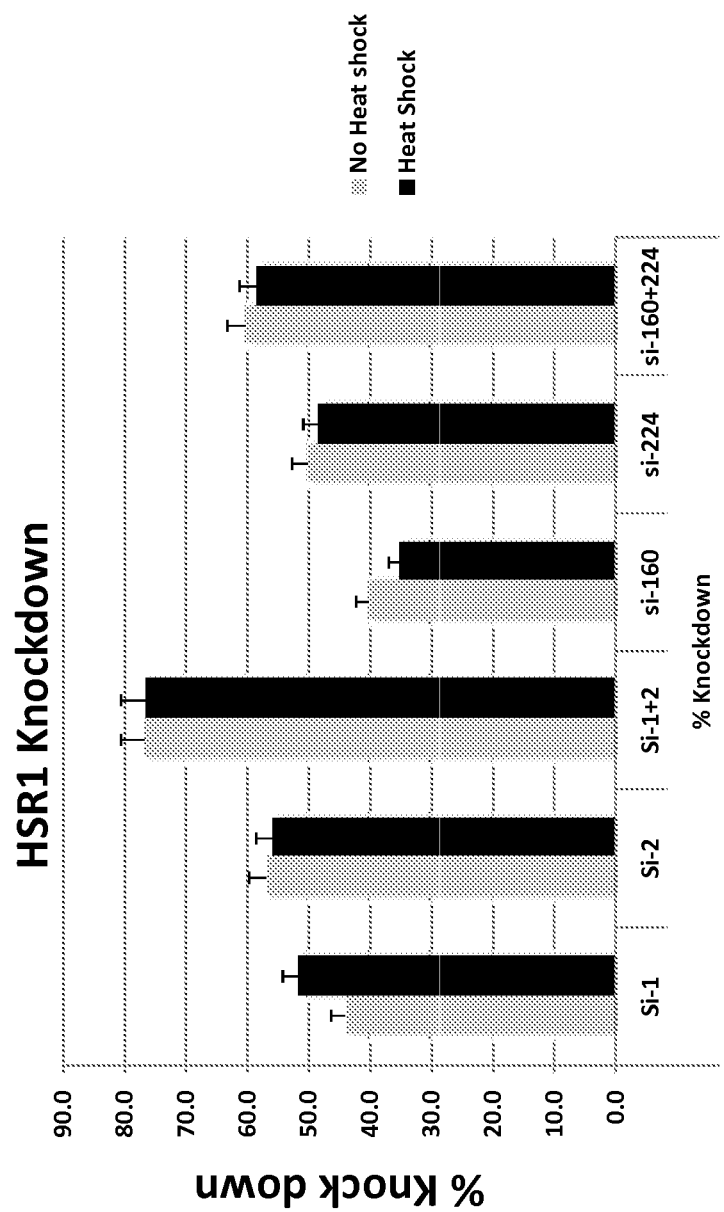
FIG. 1A shows the HSR1 inhibitory activity of siHSR1-1 and siHSR1-2, alone and in combination (compilation of data from 3 independent experiments) compared to the combination of two other siRNAs targeting HSR1 (siHSR1-160 and siHSR1-224). Lighter columns refer to cells that were not subjected to heat shock. Darker columns refer to heat shocked cells.

The present invention is based on an unexpected observation that a combination of (i) siHSR1-2 (targeting human HSR1 (SEQ ID NO: 5) nucleotides 418-444 or (SEQ ID NO: 21) nucleotides 452-474) and (ii) siHSR1-4 (targeting human HSR1 (SEQ ID NO: 5) nucleotides 26-48 or (SEQ ID NO: 21) nucleotides 56-78) or siHSR1-1 (targeting human HSR1 (SEQ ID NO: 5) nucleotides 204-230 or (SEQ ID NO: 21) nucleotides 238-260) effectively inhibits heat shock response in mammalian cells.

```
siHSR1-1
Duplex Sequences
                                            (SEQ ID NO: 1)
5'-rArUrCrUrCrCrUrArArArGrArArArUrGrArUrUrGrUrAr GrUrCrCrUrC-3'
                                            (SEQ ID NO: 2)
5'-rGrGrArCrUrArCrArArUrCrArUrUrCrUrUrUrArGrGr ArGAT-3' siHSR1-2
Duplex Sequences
                                            (SEQ ID NO: 3)
5'-rUrGrGrCrArArUrUrGrCrArArUrGrCrArGrArUrArGr CrArArGrCrC-3'

(SEQ ID NO: 4)
5'-rCrUrUrGrCrUrArUrCrUrGrCrArUrUrGrCrArArUrUr

GrCCA-3' siHSR1-4
Duplex Sequences
                                            (SEQ ID NO: 13)
5'-rGrArGrArGrUrUrArArGrGrCrArGrCrArUrCrGrUrGr CrCrUrCrCrC-3'
                                            (SEQ ID NO: 14)
5'-rGrArGrGrCrArCrGrArUrGrCrUrGrCrCrUrUrArArCr UrCTC-3'
```

The present invention is further based on an unexpected observation that antisense LNA oligonucleotide LNA HSR1-3/4 (CGCCGCCATAAGCAGA; SEQ ID NO: 6), which targets nucleotides 174-189 of human HSR1 (SEQ ID NO: 5) (correspond to nucleotides 206-221 of human HSR1 (SEQ ID NO: 21)), effectively inhibits heat shock response in mammalian cells.

```
Human (HeLa) HSR1 fragment sequence (SEQ ID NO: 5)
  1 AAAATTCGGA ACGCCCCTGT GGGGAGGCAC GATGCTGCCT TAACTCTCCG GGTGATTTCA

61 TCTTCAGCGC CGAGTGCGGA TGCACCTCGT TGAAGTGCTC GAAGGCGGCG GCCATCTGCA

121 GCACTCCTTC GGCCTGGGCC GTGTCATAGT GTGTTGCATC GACCGGTTGA ATCCGCCGCC

181 ATAAGCAGAC GTTGGAGTGG TGTGAGGACT ACAATCATTC TTTAGGAGAT GGCATTCCTC
```

```
-continued
241 CTTAAACCGC CTCACTAAGT GACGCTAATG ATGCCTACAT TGCCCCGGAG ACTGGGCTGT

301 GTAGGTGCGT TCGCCTCCAG CTTTCATCGT CCGGGTTCAT GATCTAACTC GTTGTACAGA

361 TGAAGCCACG TTTCCACCTC CATGACCAGC TTGCTGCGCT GACCTATCTA GGTCGCTGGC

421 TTGCTATCTG CATTGCAATT GCCATGCTGG TTGGCAGTGC ATCCGCCATC TTTTTGCACT

481 CGATGGAGTG GGCCACCCAA ACGCGGGACG CCAATCATTG GCTGATATGG GGACTCCCAT

541 TCGCAGGCTT CGATGTCGAC AC

Human (HeLa) HSR1 full-length sequence (SEQ ID NO: 21)
  1 CCGTCCAATT GAGGTCCGAA CCGGTTTACA CAAAAATTCG GAACGCCCCT GTGGGGAGGC

61 ACGATGCTGC CTTAACTCTC CGGGTGATTT CATCTTCAGC GCCGAGTGCG GATGCACCTC

121 GTTGAAGTGC TCGAAGGCGG CGGCCATCTG CAGCACTCCT TCGGCCTGGG CCGTGTCATA

181 GTGTGTTGCA TCGACCGGTT GAATCCGCCG CCATAAGCAG ACGTTGGAGT GGTGTGAGGA

241 CTACAATCAT TCTTTAGGAG ATGGCATTCC TCCTTAAACC GCCTCACTAA GTGACGCTAA

301 TGATGCCTAC ATTGCCCCGG AGACTGGGCT GTGTAGGTGC GTTCGCCTCC AGCTTTCATC

361 GTCCGGGTTC ATGATCTAAC TCGTTGTACA GATGAAGCCA CGTTTCCACC TCCATGACCA

421 GCTTGCTGCG CTGACCTATC TAGGTCGCTG GCTTGCTATC TGCATTGCAA TTGCCATGCT

481 GGTTGGCAGT GCATCCGCCA TCTTTTTGCA CTCGATGGAG TGGGCCACCC AAACGCGGGA

541 CGCCAATCAT TGGCTGATAT GGGGACTCCC ATTCGCAGGC TTCGATGTCG ACAC
```

1. Definitions

Within the meaning of the present invention, when used in relation to a cell of a eukaryotic organism, the terms "stress" or "stressful conditions" refer to any condition that results in activation or increase of Heat Shock Factor (HSF)-mediated transcription or in activation or increase of the synthesis of at least one heat shock protein (HSP). Examples of stressful conditions as applied to mammalian cells include without limitation elevated temperature, oxidative stress (e.g. $H_2O_2$), alcohols, hyper- and hypoosmotic stress, heavy metals, amino acid analogs, viral infection, inflammation, and serum starvation (see also Morimoto, et al., In The Biology of Heat Shock Proteins and Molecular Chaperones, 1994 (New York: Cold Spring Harbor Press), pp. 417-455).

The terms "heat shock" or "HS" or "heat stress" are used to refer to stressful conditions associated with elevated temperature (e.g., 40-43° C. for mammalian cells).

Within the meaning of the present invention, the term "inhibit" is used to refer to any level of reduction in a function or amount of a molecule. When used in connection with siRNA and LNA molecules of the invention, the term "inhibit" refers to the ability of these molecules to prevent HSR1 functioning in activating a stress response in a cell (e.g., by inducing cleavage of HSR1 [siRNA] or by preventing the formation of a secondary structure in HSR1 which is essential for HSF1 activation [LNA]).

The phrase "increasing sensitivity of a cancer cell to a treatment" is used herein to refer to any detectable decrease in propagation and/or survival of a cancer cell subjected to a given treatment.

The term "locked nucleic acid" or "LNA" as used herein refers to nucleic acid analogs with a 2'-O, 4'-C methylene bridge. This bridge restricts the flexibility of the ribofuranose ring and locks the structure into a rigid C3-endo conformation, conferring enhanced hybridization performance and exceptional biostability. LNA allows the use of very short oligonucleotides (less than 10 bp) for efficient hybridization in vivo. Reviewed in, e.g., Jepsen and Wengel, Curr. Opin. Drug Discov. Devel. 2004; 7:188-194; Crinelli et al., Curr. Drug Targets 2004; 5:745-752.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to any of the disease conditions recited herein, the terms "treat", "treatment", and the like mean to relieve or alleviate at least one symptom associated with such condition, or to slow or reverse the progression of such condition. For example, in relation to cancer, the term "treat" may mean to relieve or alleviate at least one symptom selected from the group consisting of tumor growth, metastasis, sensitivity of tumor cells to treatments such as chemotherapy, radiation therapy, thermotherapy, etc. Within the meaning of the present invention, the term "treat" also denotes to arrest, delay the onset (i.e., the period prior to clinical manifestation of a disease) and/or reduce the risk of developing or worsening a disease. Within the meaning of the present invention, disease conditions include without limitation various cancers, inflammation, HIV infection, and related disorders.

As used herein the term "therapeutically effective" applied to dose or amount refers to that quantity of a compound or pharmaceutical composition that is sufficient to result in a desired activity upon administration to an animal in need thereof. Within the context of the present invention, the term "therapeutically effective" refers to that quantity of a compound or pharmaceutical composition that is sufficient to reduce or eliminate at least one symptom of a cancer, inflammation, HIV infection, or related disorder. Note that when a combination of active ingredients is administered the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

In accordance with the present invention, there may be employed conventional molecular biology, microbiology, and recombinant DNA techniques within the skill of the art. See, e.g., Sambrook, Fritsch and Maniatis, Molecular Cloning: A Laboratory Manual, 2nd ed., Cold Spring Harbor Laboratory Press, Cold Spring Harbor, N. Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al. eds., Current Protocols in Molecular Biology, John Wiley and Sons, Inc. 1994; among others.

2. siRNA Molecules of the Invention

RNA interference (RNAi) is a process of sequence-specific post-transcriptional gene silencing by which double stranded RNA (dsRNA) homologous to a target locus can specifically inactivate gene function (Hammond et al., Nature Genet. 2001; 2:110-119; Sharp, Genes Dev. 1999; 13:139-141). This dsRNA-induced gene silencing is mediated by short double-stranded small interfering RNAs (siR-NAs) generated from longer dsRNAs by ribonuclease III cleavage (Bernstein et al., Nature 2001; 409:363-366 and Elbashir et al., Genes Dev. 2001; 15:188-200). RNAi-mediated gene silencing is thought to occur via sequence-specific RNA degradation, where sequence specificity is determined by the interaction of an siRNA with its complementary sequence within a target RNA (see, e.g., Tuschl, Chem. Biochem. 2001; 2:239-245). For mammalian systems, RNAi commonly involves the use of dsRNAs that are greater than 500 bp; however, it can also be activated by introduction of either siRNAs (Elbashir, et al., Nature 2001; 411: 494-498) or short hairpin RNAs (shRNAs) bearing a fold back stem-loop structure (Paddison et al., Genes Dev. 2002; 16: 948-958; Sui et al., Proc. Natl. Acad. Sci. USA 2002; 99:5515-5520; Brummelkamp et al., Science 2002; 296:550-553; Paul et al., Nature Biotechnol. 2002; 20:505-508).

The present invention provides siRNA molecules targeting human HSR1 (SEQ ID NO: 5) nucleotides 26-48, 204-230 and 418-444 (which correspond to human HSR1 (SEQ ID NO: 21) nucleotides 56-78, 238-260 and 452-474, respectively) or corresponding nucleotides in HSR1 orthologs in other species (e.g., mammalian orthologs from hamster or mouse). In one embodiment, such siRNA molecules comprise nucleic acid sequences that are complementary to nucleotides 26-48 and/or 204-230 and/or 418-444 of human HSR1 (SEQ ID NO: 5) (which correspond to human HSR1 (SEQ ID NO: 21) nucleotides 56-78, 238-260 and 452-474, respectively). In one specific embodiment, the siRNA molecules of the invention have the following sequences:

```
siHSR1-1
                                        (SEQ ID NO: 1)
5'-rArUrCrUrCrCrUrArArArGrArArUrGrArUrGrUrArGr

UrCrCrUrC-3'
                                        (SEQ ID NO: 2)
5'-rGrGrArCrUrArCrArArUrCrArUrUrCrUrUrUrArGrGr

ArGAT-3' siHSR1-2
                                        (SEQ ID NO: 3)
5'-rUrGrGrCrArArUrUrGrCrArArUrGrCrArGrArUrArGr

CrArArGrCrC-3'
                                        (SEQ ID NO: 4)
5'-rCrUrUrGrCrUrArUrCrUrGrCrArUrUrGrCrArArUr

UrGrCCA-3' siHSR1-4
                                        (SEQ ID NO: 13)
5'-rGrArGrArGrUrUrArArGrGrCrArGrCrArUrCrGrUrGrCr

CrUrCrCrC-3'
                                        (SEQ ID NO: 14)
5'-rGrArGrGrCrArCrGrArUrGrCrUrGrCrCrUrUrArArCr

UrCTC-3'
```

The siRNAs of the present invention are preferably short double stranded nucleic acid duplexes comprising annealed complementary single stranded nucleic acid molecules. In preferred embodiments, the siRNAs are short dsRNAs comprising annealed complementary single strand RNAs. However, the invention also encompasses embodiments in which the siRNAs comprise an annealed RNA:DNA duplex, wherein the sense strand of the duplex is a DNA molecule and the antisense strand of the duplex is a RNA molecule.

In some embodiments, duplexed siRNAs have a 2 or 3 nucleotide 3' overhang on each strand of the duplex. In some embodiments, siRNAs have 5'-phosphate and 3'-hydroxyl groups.

The siRNA molecules of the invention may include one or more modifications (e.g., to the base moiety, sugar moiety, phosphate moiety, phosphate-sugar backbone, or a combination thereof). For example, the phosphodiester linkages may be modified to include at least one heteroatom other than oxygen, such as nitrogen or sulfur. In this case, for example, the phosphodiester linkage may be replaced by a phosphothioester linkage. Similarly, bases may be modified to block the activity of adenosine deaminase. Other examples of useful modifications are morpholino modifications and LNA. Where the siRNA molecule is produced synthetically, or by in vitro transcription, a modified ribonucleoside may be introduced during synthesis or transcription.

Non-limiting examples of modified base moieties include inosine, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

Non-limiting examples of modified sugar moieties include arabinose, 2-fluoroarabinose, xylulose, and hexose. Modified siRNAs may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted sialyl; a fluorescein moiety; a reporter group; a group for improving the pharmacokinetic properties; or a group for improving the pharmacodynamic properties, and other substituents having similar properties. Modified siRNAs may also have sugar mimetics such as cyclobutyls or other carbocyclics in place of the pentofuranosyl group.

Non-limiting examples of modifications of phosphate backbone include a phosphorothioate, a phosphorodithioate, a phosphoramidothioate, a phosphoramidate, a phosphordiamidate, a methylphosphonate, a phosphotriester, an alkyl phosphotriester, and a formacetal or analog thereof, as well as chimeras between methylphosphonate and phosphodiester, short chain alkyl, or cycloalkyl intersugar linkages or short chain heteroatomic or heterocyclic intersugar linkages. Specific non-limiting examples include those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds.

Also envisioned are modified siRNA molecules having morpholino backbone structures in which the bases are linked to 6-membered morpholine rings, which are connected to other morpholine-linked bases via non-ionic phosphorodiamidate intersubunit linkages. Morpholino siRNAs are highly resistant to nucleases and have good targeting predictability (U.S. Pat. No. 5,034,506; Summerton, Biochim. Biophys. Acta 1999; 1489:141-158; Summerton and Weller, Antisense Nucleic Acid Drug Dev. 1997; 7:187-195; Arora et al., J. Pharmacol. Exp. Ther. 2000; 292:921-928; Qin et al., Antisense Nucleic Acid Drug Dev. 2000; 10:11-16; Heasman et al., Dev. Biol. 2000; 222:124-134; Nasevicius and Ekker, Nat. Genet. 2000; 26:216-220).

Another type of a useful modification is the peptide-nucleic acid (PNA) backbone: the phosphodiester backbone of the oligonucleotide may be replaced with a polyamide backbone, the bases being bound directly or indirectly to the aza nitrogen atoms of the polyamide backbone (Nielsen et al., Science 1991; 254:1497).

In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) with a 2'-O, 4'-C methylene bridge. This bridge restricts the flexibility of the ribofuranose ring and locks the structure into a rigid C3-endo conformation, conferring enhanced hybridization performance and exceptional biostability.

Modified siRNAs can include appending groups such as, e.g., peptides, or agents facilitating transport across the cell membrane (see, e.g., Letsinger et al., Proc. Natl. Acad. Sci. USA 1989; 86:6553-6556; Lemaitre et al., Proc. Natl. Acad. Sci. USA 1987; 84:648-652; PCT Publication No. WO 88/09810) or blood-brain barrier (see, e.g., PCT Publication No. WO 89/10134), etc.

According to the present invention, siRNAs may be introduced to a target cell as an annealed duplex siRNA, or as single stranded sense and antisense nucleic acid sequences that, once within the target cell, anneal to form the siRNA duplex. Alternatively, the sense and antisense strands of the siRNA may be encoded on an expression construct that is introduced to the target cell. Upon expression within the target cell, the transcribed sense and antisense strands may anneal to reconstitute the siRNA.

Although the siRNA molecules useful according to the invention preferably contain nucleotide sequences that are fully complementary to nucleotides 26-48 and/or 204-230 and/or 418-444 of human HSR1 (SEQ ID NO: 5) (which correspond to human HSR1 (SEQ ID NO: 21) nucleotides 56-78, 238-260 and 452-474, respectively) or corresponding nucleotides in HSR1 orthologs in other species (e.g., other mammalian species), 100% sequence complementarity between the siRNA and the target nucleic acid is not required to practice the invention.

HSR1-specific siRNA molecules of the invention can be further optimized (e.g., by increasing their resistance to nucleases, increasing the efficiency of their targeting to cells, increasing their sequence specificity [e.g., by introducing phosphothioate or morpholino modifications or using LNA], and reducing the size) making them even more potent in inhibition of stress response in cells.

siRNA molecules of the invention can be synthesized by standard methods known in the art, e.g., by use of an automated synthesizer. RNAs produced by such methodologies tend to be highly pure and to anneal efficiently to form siRNA duplexes. Following chemical synthesis, single stranded RNA molecules are deprotected, annealed to form siRNAs, and purified (e.g., by gel electrophoresis or HPLC). Alternatively, standard procedures may used for in vitro transcription of RNA from DNA templates carrying RNA polymerase promoter sequences (e.g., T7 or SP6 RNA polymerase promoter sequences). Efficient in vitro protocols for preparation of siRNAs using T7 RNA polymerase have been described (Donzé and Picard, Nucleic Acids Res. 2002; 30:e46; and Yu et al., Proc. Natl. Acad. Sci. USA 2002; 99:6047-6052). The sense and antisense transcripts may be synthesized in two independent reactions and annealed later, or may be synthesized simultaneously in a single reaction.

siRNA molecules may be formed within a cell by transcription of RNA from an expression construct introduced into the cell. For example, both a protocol and an expression construct for in vivo expression of siRNAs are described in Yu et al., supra.

The expression constructs for in vivo production of siRNA molecules comprise siRNA encoding sequences operably linked to elements necessary for the proper transcription of the siRNA encoding sequence(s), including promoter elements and transcription termination signals. Preferred promoters for use in such expression constructs include the polymerase-III HI-RNA promoter (see, e.g., Brummelkamp et al., supra) and the U6 polymerase-III promoter (see, e.g., Sui et al., supra; Paul, et al. supra; and Yu et al., supra). The siRNA expression constructs can further comprise vector sequences that facilitate the cloning of the expression constructs. Standard vectors that maybe used in practicing the current invention are known in the art (e.g., pSilencer 2.0-U6 vector, Ambion Inc., Austin, Tex.).

3. Use of the siRNA Molecules and Antisense Lna Oligonucleotides of the Invention in Developing Novel Cancer Treatments One of the major problems in cancer treatment today is the resistance of tumor cells to existing therapies. At least part of this resistance is due to increased synthesis of heat shock proteins (HSPs). As specified in the Background Section, supra, HSPs are synthesized in all cells in response to adverse conditions such as heat stress. They protect the cell from injury by preventing denaturation of cellular proteins and ensuring correct folding of newly synthesized polypeptides. In cancer cells, high level of HSPs prevents initiation of apoptosis, or programmed cell death, in response to therapeutic treatment. Indeed, as described in Tang et al. (Cell Stress and Chaperones 2005; 10:46-58), HSF and HSP levels are elevated in more highly malignant prostate carcinoma cells. As the synthesis of HSPs in response to stress is controlled by transcription factor HSF, finding a way to inhibit HSF activation in cancer cells will result in increasing efficiency of existing anti-cancer treatments. As further discussed in the Background Section, the activation of HSF in response to heat stress requires at least two additional components: translation elongation factor eEF1A and Heat Shock RNA (HSR1). These two components act together to activate HSF.

The present invention provides novel anti-cancer agents based on the HSR1-targeted siRNA molecules and antisense LNA oligonucleotides as well as methods for using such siRNA molecules and antisense LNA oligonucleotides to treat cancer. The novel anti-cancer siRNAs and antisense LNA oligonucleotides of the present invention can be used in conjunction with existing treatments to improve their effect by increasing the sensitivity of the cells to pro-apoptotic stimuli such as thermo-, chemo-, and radiotherapeutic treatments.

In conjunction with the siRNA and antisense LNA oligonucleotide therapeutics of the invention, the present invention also provides a method for treating cancer in a mammal comprising administering said therapeutics to the mammal. In a specific embodiment, the mammal is human. In another specific embodiment, the method further comprises subjecting the mammal to a treatment selected from the group consisting of radiation therapy, chemotherapy, thermotherapy, and any combination thereof.

Similarly, the present invention provides a method for increasing sensitivity of a cancer cell to an anti-cancer treatment (e.g., radiation treatment, chemical treatment, thermal treatment, or any combination thereof) and thus improving efficiency of such anti-cancer treatment in a mammal comprising administering to the mammal the siRNA and/or antisense LNA oligonucleotide therapeutics of the invention. The relative timing of siRNA/antisense LNA administration and anti-cancer treatment would depend on the delivery mechanism for siRNA/antisense LNA and on the type of the specific anti-cancer treatment used. Generally, cells may become more sensitive to an anti-cancer treatment as soon as one hour after siRNA/antisense LNA administration.

Cancers treatable using the methods of the present invention include without limitation fibrosarcoma, myxosarcoma, liposarcoma, chondrosarcoma, osteogenic sarcoma, chordoma, angiosarcoma, endotheliosarcoma, lymphangiosarcoma, lymphangioendothelio-sarcoma, synovioma, mesothelioma, Ewing's tumor, leiomyosarcoma, rhabdomyosarcoma, colon carcinoma, pancreatic cancer, breast cancer, ovarian cancer, prostate cancer, lymphoma, leukemia, squamous cell carcinoma, basal cell carcinoma, adenocarcinoma, hepatocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, among others.

As disclosed above, the anti-cancer siRNA- and LNA antisense oligonucleotide-containing compositions of the present invention are advantageously used in combination with other treatment modalities, including without limitation radiation, chemotherapy, and thermotherapy.

Chemotherapeutic agents used in the methods of the present invention include without limitation taxol, taxotere and other taxoids (e.g., as disclosed in U.S. Pat. Nos. 4,857,653; 4,814,470; 4,924,011, 5,290,957; 5,292,921; 5,438,072; 5,587,493; European Patent No. EP 253 738; and PCT Publication Nos. WO 91/17976, WO 93/00928, WO 93/00929, and WO 96/01815), cisplatin, carboplatin, (and other platinum intercalating compounds), etoposide and etoposide phosphate, bleomycin, mitomycin C, CCNU, doxorubicin, daunorubicin, idarubicin, ifosfamide, methotrexate, mercaptopurine, thioguanine, hydroxyurea, cytarabine, cyclophosphamide, nitrosoureas, mitomycin, dacarbazine, procarbizine, campathecins, dactinomycin, plicamycin, mitoxantrone, asparaginase, vinblastine, vincristine, vinorelbine, paclitaxel, docetaxel, calicheamicin, and the like.

Typical radiation therapy used in the methods of the invention includes without limitation radiation at 1-2 Gy.

Also encompassed by the present invention is radiation therapy and chemotherapy via local delivery of radioconjugates and chemotherapeutics, respectively. Directing the cytotoxic exposure directly to the tumor itself is a commonly used approach to deliver a cytotoxic drug while minimizing the cytotoxic exposure of normal tissues. However, one of the factors which limit the effectiveness of such an approach is incomplete induction of tumor cell death because of limited dose delivery. Thus, it would be highly desirable to concurrently use the HSR1-specific therapeutics of the invention to enhance the sensitivity of the tumor cells to the particular cytotoxic agent. Tumor-specific delivery is commonly achieved by conjugating a cytotoxic agent (e.g., a toxins (such as ricin) or a radioisotope) to an antibody that preferentially targets the tumor (e.g., anti-CD2 in neuroblastoma or anti-Her2-neu in certain breast carcinomas). The targeting may be also done with natural targeting (i.e., with radioactive iodine in the treatment of thyroid carcinoma), physical targeting (i.e., administration of a radioisotope to a particular body cavity), or other targeting protein (e.g., ferritin in hepatocellular carcinoma).

In addition to combination with conventional cancer therapies such as chemotherapy, radiation therapy, thermotherapy, and surgery (tumor resection), HSR1-targeted therapy of a tumor using siRNAs of the invention can be combined with other anti-tumor therapies, including but by no means limited to suicide gene therapy (i.e., introduction of genes that encode enzymes capable of conferring to tumor cells sensitivity to chemotherapeutic agents such as thymidine kinase of herpes simplex virus or varicella zoster virus and bacterial cytosine deaminase), anti-oncogene or tumor suppressor gene therapy (e.g., using anti-oncogene molecules including monoclonal antibodies, single chain antibody vectors, antisense oligonucleotide constructs, ribozymes, immunogenic peptides, etc.), administration of tumor growth inhibitors (e.g., interferon (IFN)-γ, tumor necrosis factor (TNF)-α, TNF-β, and similar cytokines, antagonists of tumor growth factor (TGF)-β and IL-10, etc.), administration of angiogenesis inhibitors (e.g., fragments of angiogenic proteins that are inhibitory [such as the ATF of urokinase], angiogenesis inhibitory factors [such as angiostatin and endostatin], tissue inhibitors of metalloproteinase, soluble receptors of angiogenic factors [such as the urokinase receptor or FGF/VEGF receptor], molecules which block endothelial cell growth factor receptors, and Tie-1 or Tie-2 inhibitors), vasoconstrictive agents (e.g., nitric oxide inhibitors), immune therapies with an immunologically active polypeptide (including immunostimulation, e.g., in which the active polypeptide is a cytokine, lymphokine, or chemokine [e.g., IL-2, GM-CSF, IL-12, IL-4], and vaccination, in which the active polypeptide is a tumor specific or tumor associated antigen), and the like.

4. Use of the siRNA Molecules and Antisense Lna Oligonucleotides of the Invention in Developing Novel Anti-Inflammatory Agents As specified in the Background Section, supra, HSPs, and HSP70 family in particular, is considered a part of a protective mechanism against inflammation (Jattela et al., EMBO J. 1992; 11:3507-3512; Morris et al., Int. Biochem. Cell Biol. 1995; 27:109-122; Ianaro et al., FEBS Lett. 2001; 499:239-244; Van Molle et al., Immunity 2002; 16:685-695; Ianaro et al., Mol. Pharmacol. 2003; 64:85-93; Ianaro et al., FEBS Lett. 2001; 499:239-244; Ianaro et al., FEBS Lett. 2001; 508:61-66). It follows, that selective HSF-mediated transcriptional activation of HSP genes may lead to remission of the inflammatory reaction.

As disclosed above, the HSR1-targeted siRNA molecules and antisense LNA oligonucleotides of the invention can be used to inhibit heat shock response in cells and in this way provide a basis for developing novel anti-inflammatory therapeutics.

The anti-inflammatory activity of the HSR1-specific siRNA molecules and antisense LNA oligonucleotides of the invention can be assessed using various methods known in the art, including without limitation, measurement of inflammatory cytokines (such as TNF-α, IL-1, IFN-γ), measurement of activated immune system cells (e.g., measurement of the invasion or accumulation in an organ or tissue of proinflammatory lymphoid cells or the presence locally or peripherally of activated pro-inflammatory lymphoid cells recognizing a pathogen or an antigen specific to the organ or tissue) as well as observation (reduction of erythema/redness, reduction of elevated body/tissue temperature, reduction of swelling/edema, reduction of pain in the affected area, reduction of pruritus or burning sensation, improvement in function of the afflicted organ).

In conjunction with the siRNA and antisense LNA therapeutics of the invention, the present invention also provides a method for inhibiting an inflammatory reaction in a mammal comprising administering said therapeutics to the mammal. In a specific embodiment, the mammal is human.

The siRNAs and antisense LNA oligonucleotides of the invention can be used in the prophylaxis as well as in the therapeutic treatment of several disorders (diseases and other pathological inflammatory conditions) caused by or associated with an abnormal or undesirable (excessive, nonregulated, or deregulated) inflammatory immune response involving the production of inflammatory cytokines or other inflammation mediators, including without limitation TNF-α and IL-1β. They include autoimmune diseases such as rheumatoid arthritis, insulin-dependent diabetes mellitus, autoimmune thyroiditis, multiple sclerosis, uveoretinitis, lupus erythematosus, scleroderma; other arthritic conditions having an inflammatory component such as rheumatoid spondylitis, osteoarthritis, septic arthritis and polyarthritis; other inflammatory brain disorders, such as meningitis, Alzheimer's disease, AIDS dementia encephalitis, other inflammatory eye inflammations, such as retinitis; inflammatory skin disorders, such as, eczema, other dermatites (e.g., atopic, contact), psoriasis, burns induced by UV radiation (sun rays and similar UV sources); inflammatory bowel disease, such as Crohn's disease, ulcerative colitis; asthma; other allergy disorders, such as allergic rhinitis; conditions associated with acute trauma such as cerebral injury following stroke, heart tissue injury due to myocardial ischemia, lung injury such as that which occurs in adult respiratory distress syndrome; inflammation accompanying infection, such as sepsis, septic shock, toxic shock syndrome, other inflammatory conditions associated with particular organs or tissues, such as nephritis (e.g., glomerulonephritis), inflamed appendix, gout, inflamed gall bladder, chronic obstructive pulmonary disease, congestive heart failure, Type II diabetes, lung fibrosis, vascular disease, such as atherosclerosis and restenosis; and alloimmunity leading to transplant rejection.

The anti-inflammatory siRNAs and antisense LNA oligonucleotides of the present invention can be used in conjunction with existing therapeutics such as inhibitors of TNF-α, inhibitors of COX-1/COX-2, inhibitors of IL-1β, etc. In a specific embodiment, the siRNAs of the invention are administered in combination with Non-Steroidal Anti-Inflammatory Drugs (NSAIDs). Suitable NSAIDs include, but are not limited to, those which inhibit cyclooxygenase, the enzyme responsible for the biosyntheses of the prostaglandins and certain autocoid inhibitors, including inhibitors of the various isoenzymes of cyclooxygenase (including, but not limited to, cyclooxygenase-1 and -2), and as inhibitors of both cyclooxygenase and lipoxygenase relates to NSAID, such as the commercially available NSAIDs aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celecoxib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acethyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine. Additional NSAID genera and particular NSAID compounds are disclosed in U.S. Pat. No. 6,297,260 and International Patent Application No. WO 01/87890.

5. Use of the siRNA Molecules and Antisense Lna Oligonucleotides of the Invention in Developing Novel Anti-Hiv Therapeutics As disclosed in the Background Section, above, the HSR1-specific siRNAs and antisense LNA oligonucleotides of the invention can be used as therapeutics to treat HIV infection.

In conjunction with the siRNA and antisense LNA therapeutics of the invention, the present invention also provides a method for inhibiting HIV transcription in a mammal comprising administering said therapeutics to the mammal. In a specific embodiment, the mammal is human.

The siRNA and antisense LNA therapeutics of the present invention can be used in conjunction with existing anti-HIV therapeutics such as azidothimidine (AZT), non-nucleotide analog inhibitors of reverse transcriptase, such as Nevirapine (BI-RG-587), TIBO (R82913), pyrinodes (such as R-697,661 and L-696,227), bis(heteroaryl) piperazines (BHAPs, such as U-87201E and U-90,152), atevirdine mesylate (ATV) and R-89431; HIV protease inhibitors, including substrate analogs and non-analogs, such as Ro 31-8959, A-77003 and A-80987; HIV Tat protein inhibitors, such as Ro 5-3335 and Ro 27-7429; blockers of viral entry into cells, such as soluble CD4 protein (sCD4), and chimeric sCD4 derivatives, such as CD4-IgG and CD4-PE40; blockers of HIV RNaseH activity, such as the AZT derivative azidothymidine monophosphate; drugs that alter the intracellular milieu to create conditions less favorable for viral replication, such as the free-radical scavengers and glutathione-level restoring drugs (N-acetylcysteine and similar drugs), thalidomine, etc.

6. Examples

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

(i) Cell Culture and Heat Shock Treatment

HeLa cells (ATCC Accession No. CCL-2) and BHK-21 cells (ATCC Accession No. CRL-1632), MDA MB-231 cells (ATCC Accession No. HTB-26), TIG1 cells (JCRB0501), and PL45 cells (ATCC Accession No. CRL-2558) were grown at 37° C. in an incubator with 5% $CO_2$. HeLa, MDA MB-231 cells, TIG1 cells, and PL45 cells cells were grown in DMEM containing 10% FBS, 2 mM glutamine and antibiotic/antimycotic cocktail (penicillin/streptomycin/fungizone). BHK-21 cells were maintained in DMEM/F-12 (1:1) mixture supplemented with 10% NBCS, 2 mM glutamine and the same antibiotic cocktail. Heat shock of cultured cells was performed in a water bath adjusted to 43° C. or 45° C. as indicated in the descriptions of figures and related examples. Monolayer cells grown in screw-cap flasks were tightly closed, sealed with parafilm and submerged in the water bath for indicated time periods as indicated in the legends. Corresponding control cells were maintained in tightly closed flasks in the incubator at 37° C.

MRC9 cells (ATCC Accession No. CCL-212) were grown in Gibco Minimum Essential Media containing 10% FBS, 2 mM glutamine, non-essential aminoacids and antibiotic cocktail (penicillin/streptomycin). Heat shock of cultured cells was performed in a water bath adjusted to 43° C. Monolayer cells grown in screw-cap flasks were tightly closed, sealed with parafilm and submerged in the water bath for indicated time periods. Corresponding control cells were maintained in tightly closed flasks in the incubator at 37° C.

(ii) siRNA Experiments

The following siRNA molecules were used:

```
siHSR1-1(targets human HSR1 (SEQ ID NO: 5)
nucleotides 204-230 or (SEQ ID NO: 21) nucleotides
238-260)

(SEQ ID NO: 1)
5'-AUCUCCUAAAGAAUGAUUGUAGUCCUC-3'

(SEQ ID NO: 2)
3'-TAGAGGAUUUCUUACUAACAUCAGG-5' siHSR1-2 (targets human HSR1 (SEQ ID NO: 5)
nucleotides 418-444 or (SEQ ID NO: 21) nucleotides
452-474)

(SEQ ID NO: 3)
5'-AGGCAAUUGCAAUGCAGAUAGCAAGCC-3'

(SEQ ID NO: 3)
3'-ACCGUUAACGUUACGUCUAUCGUUC-5' siHSR1-4 (targets human HSR1 (SEQ ID NO: 5)
nucleotides 26-48 or (SEQ ID NO: 21) nucleotides
56-78)

(SEQ ID NO: 13)
5'-GAGAGUUAAGGCAGCAUCGUGCCUCCC-3'

(SEQ ID NO: 14)
3'-CTCUCAAUUCCGUCGUAGCACGGAG-5'
```

-continued

HSR1-5 (targets human HSR1 (SEQ ID NO: 5)
nucleotides 84-106 or (SEQ ID NO: 21) nucleotides
114-136)

(SEQ ID NO: 15)
5'-GCCUUCGAGCACUUCAACGAGGUGCAU-3'

(SEQ ID NO: 16)
3'-CGGAAGCUCGUGAAGUUGCUCCACG-5'

HSR1-6 (targets human HSR1 (SEQ ID NO: 5)
nucleotides 182-204 or (SEQ ID NO: 21) nucleotides
212-234)

(SEQ ID NO: 17)
5'-CACACCACUCCAACGUCUGCUUAUGGC-3'

(SEQ ID NO: 18)
3'-GTGUGGUGAGGUUGCAGACGAAUAC-5'

HSR1-7 (targets human HSR1 (SEQ ID NO: 5)
nucleotides 143-165 or (SEQ ID NO: 21) nucleotides
173-195)

(SEQ ID NO: 19)
5'-CGGUCGAUGCAACACACUAUGACACGG-3'

(SEQ ID NO: 20)
3'-GCCAGCUACGUUGUGUGAUACUGUG-5' siHSR160 (targets human HSR1 (SEQ ID NO: 5)
nucleotides 129-155 or (SEQ ID NO: 21) nucleotides
164-186)

(SEQ ID NO: 7)
5'-CAACACACUAUGACACGGCCCAGGCCG-3'

(SEQ ID NO: 8)
3'-GTUGUGUGAUACUGUGCCGGGUCCG-5' siHSR224 (targets human HSR1 (SEQ ID NO: 5)
nucleotides 187-213 or (SEQ ID NO: 21) nucleotides
222-244)

(SEQ ID NO: 9)
5'-UUGUAGUCCUCACACCACUCCAACGUC-3'

(SEQ ID NO: 10)
3'-AACAUCAGGAGUGUGGUGAGGUUGC-5'

Non-target (scrambled) siRNA (SEQ ID NO: 11)
5'-GUGUCAUGAUCUCCUAAUCCGAUAUAA-3'

(SEQ ID NO: 12)
5'-GUCCAAUCCAGGAGUCGGUAGAAATA-3'

HSR1 inhibitory activity of siHSR1-1 and siHSR1-2, alone and in combination was assed and compared to HSR1 inhibitory activity of the combination of two other siRNAs targeting HSR1 (siHSR160 and siHSR224). MDA-MB231 cells were transfected with the tested individual siRNAs or their combinations. 24 hrs after transfection, cells were heatshocked at 43° C. for 30 minutes and RNA was isolated. The RNA was subjected to reverse transcription followed by QPCR. The quantification was done as follows: the Ct Values for HSR1 amplification were normalized against 18srRNA; ΔΔCt values were calculated by comparing specific siRNA treated samples to non-target (scrambled) siRNA treated samples. An average of 77% knockdown of HSR1 was achieved when a combination of siHSR1-1 and siHSR1-2 was used, as compared to 60% knockdown when a combination of siHSR160 and siHSR224 was used (FIG. 1A).

Figure 1B:
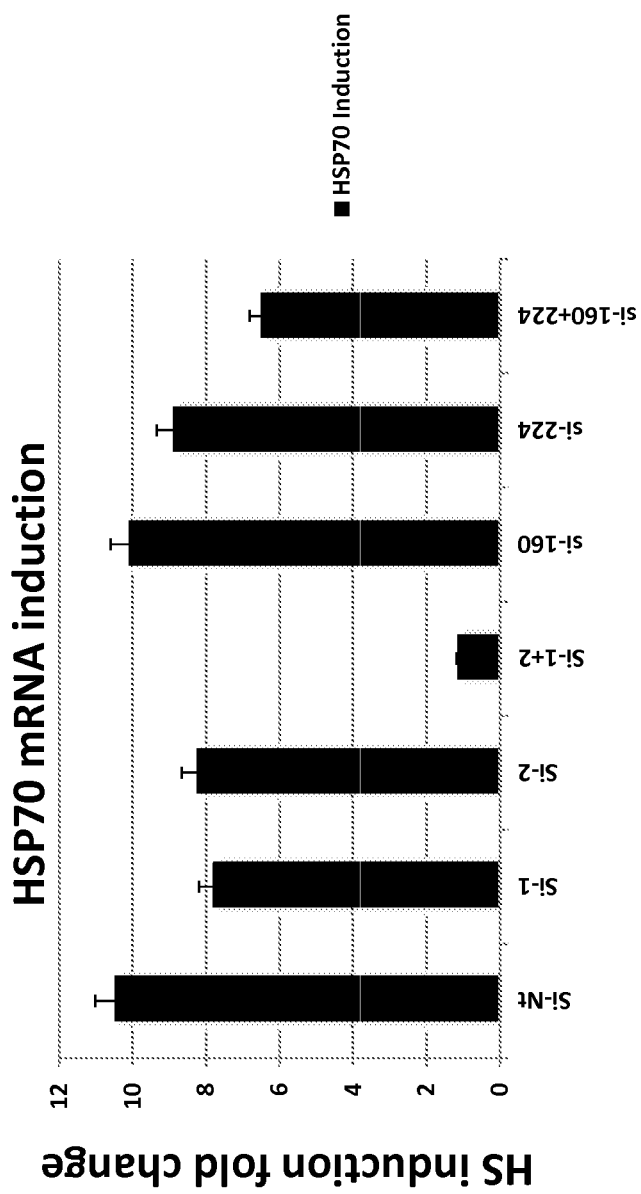
FIG. 1B shows quantification of fold change in HSP70 mRNA induction upon heat shock, in samples treated with siHSR1-1 and siHSR1-2, alone or in combination as compared to the combination of two other siRNAs targeting HSR1 (siHSR1-160 and siHSR1-224) (compilation of data from 3 independent experiments).

The present inventors have also performed quantification of a change in HSP70 mRNA induction upon heat shock, in samples treated with siHSR1-1 and siHSR1-2, individually or in combination. The effect of siHSR1-1 and siHSR1-2 was compared to the effect of siHSR160 and siHSR224. The cells were transfected with siRNAs. 24 hrs after transfection, cells were heatshocked at 43° C. for 30 minutes followed by 30 minutes recovery at 37° C. and RNA was isolated. The RNA was subjected to reverse transcription followed by QPCR. The calculation was as follows: Ct Values of HSP70 mRNA amplification were normalized to 18S rRNA; ΔΔCt was calculated by comparing heatshocked samples to non-heatshocked samples; fold change was calculated using formula, $2^{-\Delta\Delta Ct}$. When using a combination of siHSR1-1 and siHSR1-2 a 9-fold reduction in HSP70 mRNA induction upon heat shock was achieved, as compared to a 4 fold reduction in HSP70 mRNA induction in the presence of a combination of siHSR160 and siHSR224 (FIG. 1B). This result indicates a powerful synergistic effect of the combination of siHSR1-1 and siHSR1-2 in impairing HSP70 mRNA production upon stress. The 9-fold reduction in HSP70 mRNA achieved with the combination of siHSR1-1 and siHSR1-2 can lead to complete loss of HSP70 protein production.

The present inventors have also performed quantification and comparison of a change in HSP70 mRNA induction upon heat shock, in MRC9 cells treated with siHSR1-1, 2, 4, 5, 6, 7, individually or in various pair-wise combinations. The cells were transfected with siRNAs. 24 hrs after transfection, cells were heatshocked at 43° C. for 30 minutes and RNA was isolated. The RNA was subjected to reverse transcription followed by qPCR. The calculation was as follows: Ct Values of HSP70 mRNA amplification were normalized to 18S rRNA; ΔΔCt was calculated by comparing heatshocked samples to non-heatshocked samples; fold change was calculated using formula, $2^{-\Delta\Delta Ct}$.

Figure 3A:
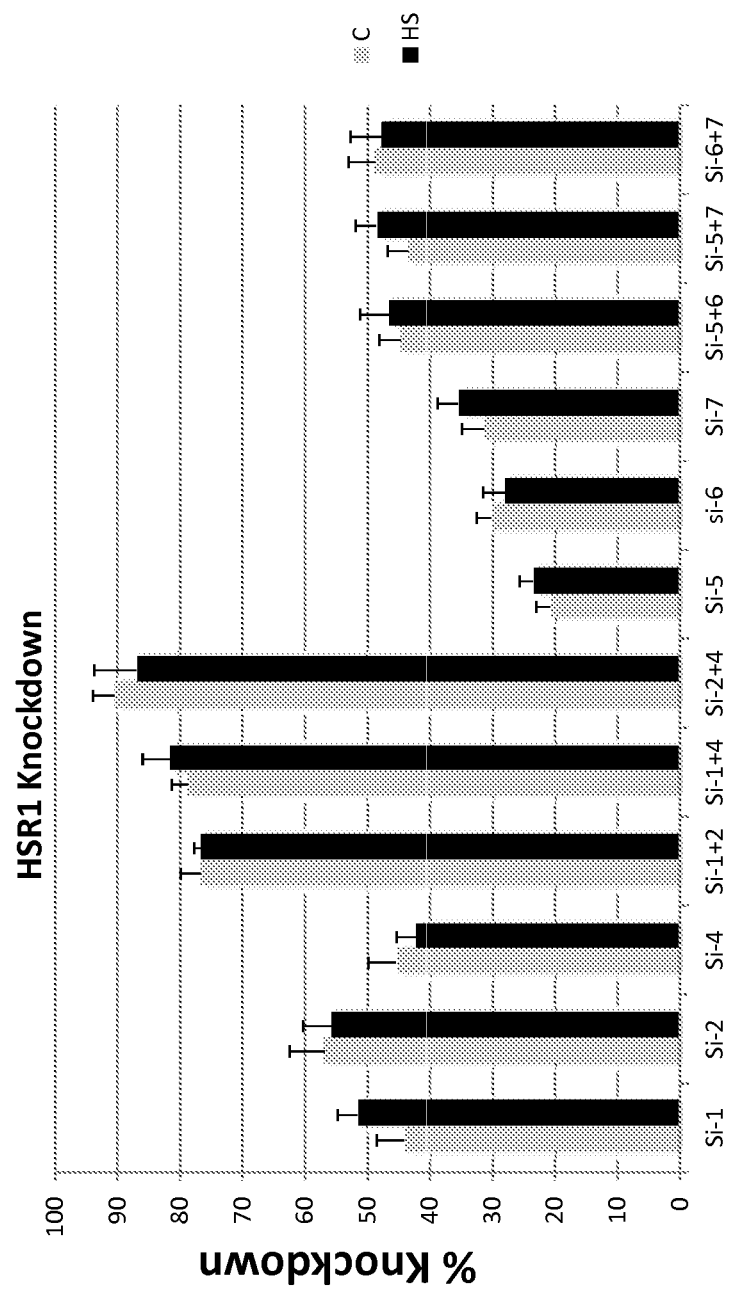
FIG. 3A shows HSR1 inhibitory activity of siHSR1-1, 2, 4, 5, 6, 7, alone and in various pair-wise combinations (compilation of data from 3 independent experiments). Lighter columns refer to cells that were not subjected to heat shock. Darker columns refer to heat shocked cells.

An average % knockdown of HSR1 was as follows (FIG. 3A):
siHSR1-2+siHSR1-4: %; NoHS-90.56, HS-86.98
siHSR1-1+siHSR1-4: %; NoHS-78.8, HS-81.5
siHSR1-1+siHSR1-2: %; NoHS-76.7, HS-76.7
siHSR1-1 alone: %; NoHS-44.1, HS-51.6
siHSR1-2 alone: %; NoHS-56.9, HS-55.8
siHSR1-4 alone: %; NoHS-45.56, HS-42.16
siHSR1-5+siHSR1-6: %; NoHS-44.7, HS-46.67
siHSR1-5+siHSR1-7: %; NoHS-43.56, HS-48.65
siHSR1-6+siHSR1-7: %; NoHS-48.88, HS-47.67
siHSR1-5 alone: %; NoHS-20.85, HS-23.56
siHSR1-6 alone: %; NoHS-30.22, HS-28.14
siHSR1-7 alone: %. NoHS-31.35, HS-35.5

Figure 3B:
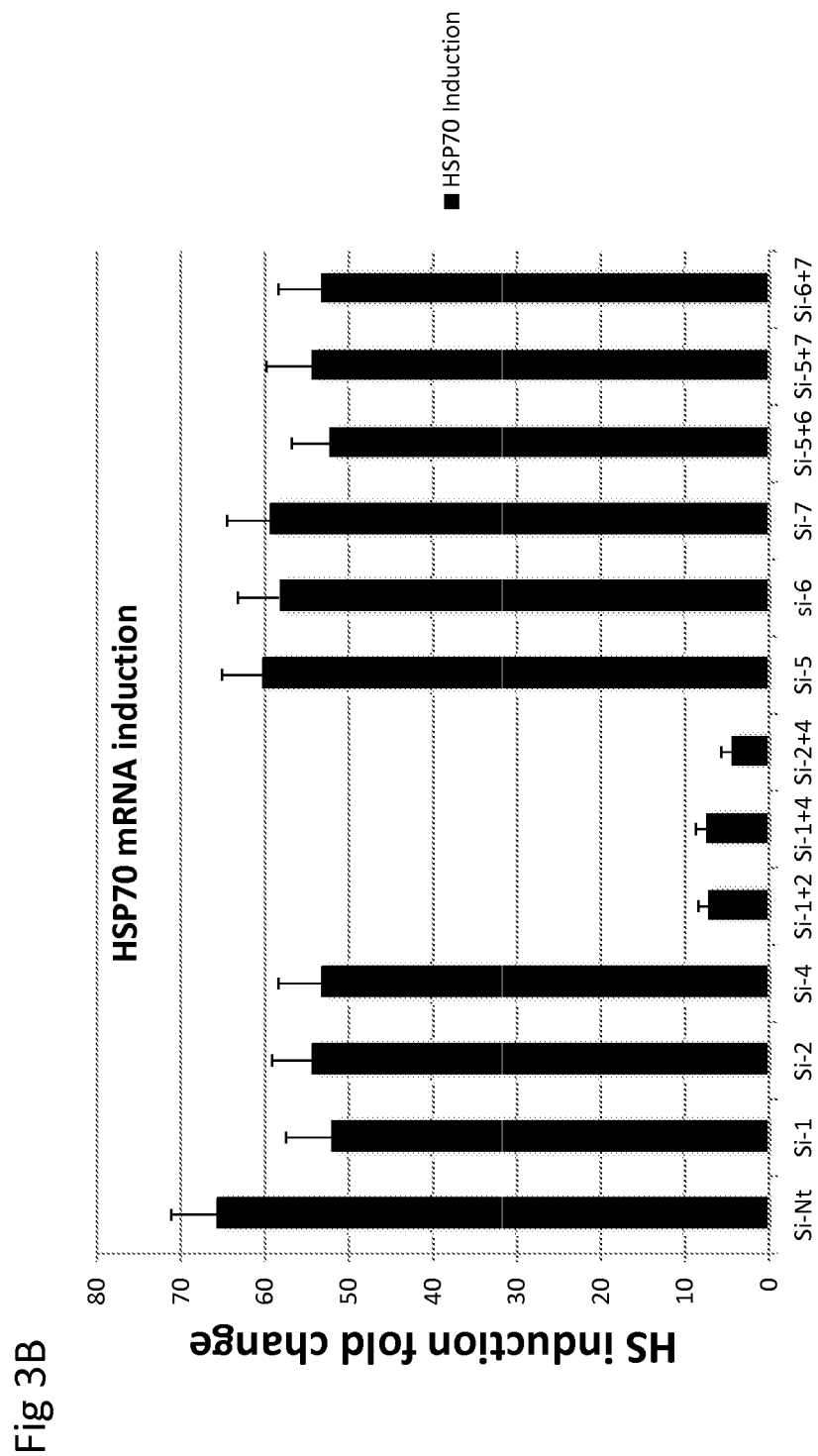
FIG. 3B shows quantification of fold change in HSP70 mRNA induction upon 30 minutes heat shock, in samples treated with siHSR1-1, 2, 4, 5, 6, 7, alone and in various pair-wise combinations (compilation of data from 3 independent experiments).

When using a combination of siHSR1-1 and siHSR1-4, a 9-fold reduction in HSP70 mRNA induction upon heat shock was achieved. Combination of siHSR1-1 and siHSR1-2 also lead to 9.2-fold reduction in HSP70 mRNAinduction upon heat shock. By using a combination of siHSR1-2 and siHSR1-4 a 15-fold reduction in HSP70 mRNA induction upon heat shock was achieved. These values are significantly higher as compared to a 1.25-, 1.2-, and 1.23-fold reduction in HSP70 mRNA induction in the presence of a combination of siHSR1-(5+6), siHSR1-(5+7), and siHSR1-(6+7) respectively (FIG. 3B). This result indicates a powerful synergistic effect of siHSR1-1, siHSR1-2 and siHSR1-4 in inhibiting HSR1 and impairing HSP70 mRNA production upon stress. The 15-fold reduction in HSP70 mRNA induction upon heat shock achieved with the combination of siHSR1-2 with siHSR1-4 and the 9-fold reduction in HSP70 mRNA induction upon heat shock achieved with the combinations of (i) siHSR1-1 with siHSR1-2 or (ii) siHSR1-1 with siHSR1-4 can lead to an essentially complete inhibition of HSP70 protein production (FIG. 3C) and thus an essentially complete inhibition of a stress response in a cell.

An average fold reduction in heat shock induced Hsp70 mRNA expression was as follows (FIG. 3B):
siHSR1-2+siHSR1-4: 15
siHSR1-1+siHSR1-4: 9
siHSR1-1+siHSR1-2: 9.2
siHSR1-1 alone: 1.26
siHSR1-2 alone: 1.2
siHSR1-4 alone: 1.25
siHSR1-5+siHSR1-6: 1.25
siHSR1-5+siHSR1-7: 1.2
siHSR1-6+siHSR1-7: 1.23
siHSR1-5 alone: 1.08
siHSR1-6 alone: 1.12
siHSR1-7 alone: 1.10

Figure 3C:
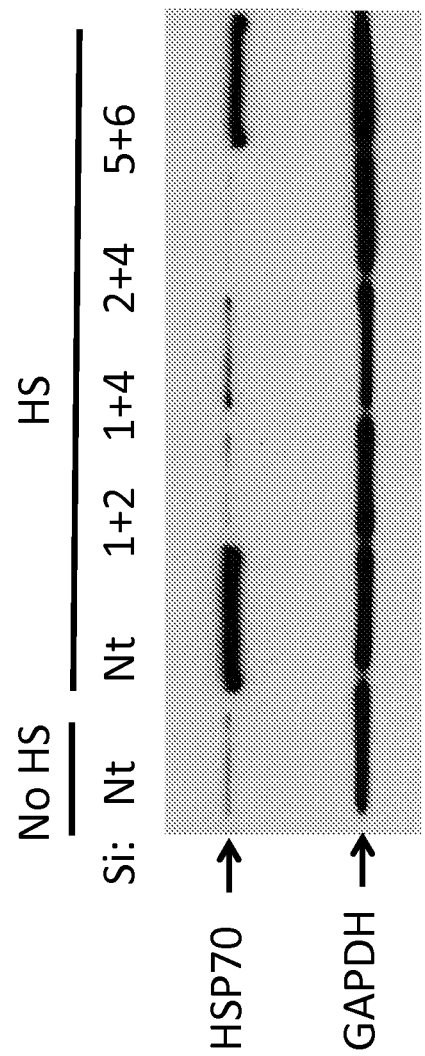
FIG. 3C shows Western blot analysis of HSP70 protein induction upon heat shock in nontransformed human fibroblasts (MRC9) treated with siHSR1-1, 2, 4, 5, 6 in various pair-wise combinations.

To assess the effect of pair-wise combinations of siHSR1-1, siHSR1-2 and siHSR1-4 on HSP70 protein induction upon heat shock, nontransformed human fibroblast (MRC9) cells were transfected with Non-target siRNA (SiNt) (DS NC1 from IDT), siHSR1-(1+2), siHSR1-(1+4) and siHSR1-(2+4). After 48 hrs, the transfected cells were heatshocked at 43° C. for an hour. The cells were then recovered for 6 hrs at 37° C., lysed and the proteins were assayed by Western blot. The antibody ADI-SPA-810-F (Stressgen) was used to detect inducible HSP70 protein and GAPDH antibody ab9485 (Abcam) was used to detect GAPDH as a loading control. HSP70 protein production was diminished to levels of non-heatshocked conditions, in samples treated with siHSR1-(1+2), siHSR1-(1+4) and siHSR1-(2+4) but not with siHSR1-(5+6) (FIG. 3C).

(iii) LNA Experiments

In LNA experiments, nontransformed human fibroblast (TIG1) and pancreatic cancer cells (PL45) were transfected in 12-well plates with 0.1 µM or 0.5 µM LNA antisense oligonucleotide LNA HSR1-3/4 (CGCCGC-CATAAGCAGA; SEQ ID NO: 6; synthesized by Integrated DNA Technologies), which targets human HSR1 (SEQ ID NO: 5) nucleotides 174-189 (correspond to nucleotides 206-221 of human HSR1 (SEQ ID NO: 21)). The transfection was conducted using Lipofectamine reagent (Invitrogen) according to manufacturer's instructions. Cells were incubated with the transfection complexes for 24 hours, heat shocked for 1 hr at 43° C. and allowed to recover at 37° C. for 6 hrs. Toxicity was measured by MTT assay (Journal of Immunological Methods 1983-12-16).

Figure 2A:
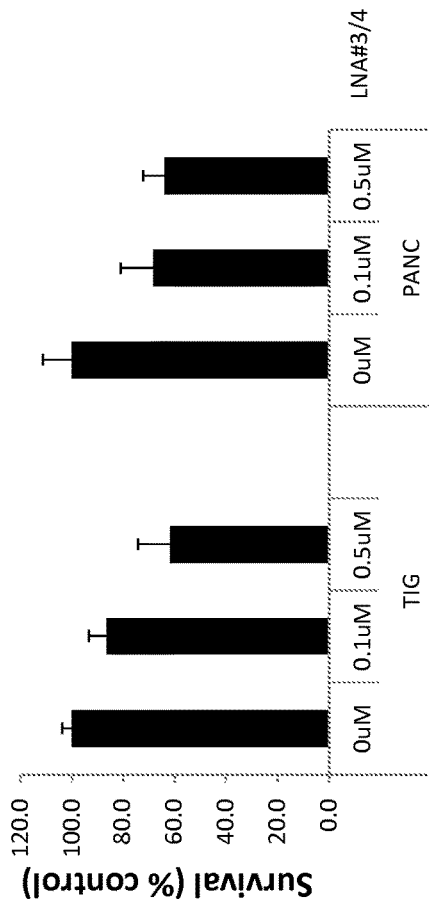
FIG. 2A shows survival of nontransformed human fibroblasts (TIG1) and pancreatic cancer cells (PANC) after tranfection with LNA oligonucleotide HSR1-3/4 at concentrations 0, 0.1 µM, and 0.5 µM. The survival was measured by MTT assay.
Figure 2B:
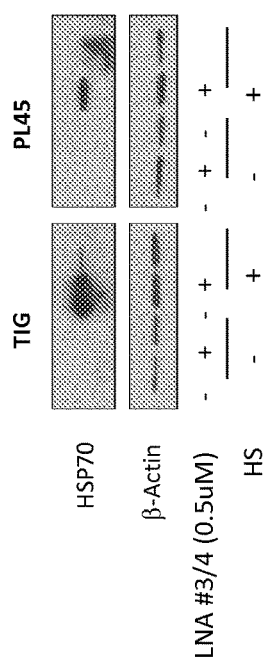
FIG. 2B shows western blot analysis of HSP70 protein induction upon heat shock in nontransformed human fibroblasts (TIG1) and pancreatic cancer cells (PL45) treated with 0.5 µM LNA oligonucleotide HSR1-3/4.

The survival of nontransformed human fibroblast (TIG1) and pancreatic cancer cells PANC was decreased by 40% when treated with LNA HSR1-3/4 (FIG. 2A).

To assess the effect of LNA HSR1-3/4 on HSP70 protein induction upon heat shock, nontransformed human fibroblast (TIG1) and pancreatic cancer cells PL45 were transfected with 0.5 µM LNA HSR1-3/4 and 24 hrs later, heat-shocked at 43° C. for an hour. The cells were then recovered for 6 hrs at 37° C., lysed and the proteins were assayed by western blot. As compared to untransfected samples, HSP70 protein production was diminished by 10 times in samples treated with LNA HSR1-3/4.

(iv) Discussion

Heat shock proteins (Hsps) are overexpressed in a wide range of human cancers. Hsp levels are biomarkers for carcinogenesis in some tissues and signal the degree of differentiation and the aggressiveness of some cancers. Several Hsp are implicated with the prognosis of specific cancers, most notably Hsp27, whose expression is associated with poor prognosis in gastric, liver, and prostate carcinoma, and osteosarcomas, and Hsp70, which is correlated with poor prognosis in breast, endometrial, uterine cervical, and bladder carcinomas. Increased Hsp expression may also predict the response to some anticancer treatments. For example, Hsp27 and Hsp70 are implicated in resistance to chemotherapy in breast cancer, Hsp27 predicts a poor response to chemotherapy in leukemia patients. The ability of the combinations of siHSR1-1, siHSR1-2 and siHSR1-4 or LNA antisense oligonucleotide LNA HSR1-3/4 to inhibit HSP expression in cancer cells indicates that these molecules can be useful in anti-cancer treatments (e.g., to sensitize cancer cells to chemotherapy or radiotherapy).

* * *

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

LIST OF SEQUENCES

| SEQUENCE | SEQ ID NO: |
|---|---|
| AUCUCCUAAAGAAUGAUUGUAGUCCUC | 1 |
| GGACUACAAUCAUUCUUUAGGAGAU | 2 |
| UGGCAAUUGCAAUGCAGAUAGCAAGCC | 3 |
| CUUGCUAUCUGCAUUGCAAUUGCCA | 4 |
| AAAATTCGGAACGCCCCTGTGGGGAGGCACGATGCTGCCTTAACTCTC CGGGTGATTTCATCTTCAGCGCCGAGTGCGGATGCACCTCGTTGAAGT GCTCGAAGGCGGCGGCCATCTGCAGCACTCCTTCGGCCTGGGCCGTGT CATAGTGTGTTGCATCGACCGGTTGAATCCGCCGCCATAAGCAGACGT TGGAGTGGTGTGAGGACTACAATCATTCTTTAGGAGATGGCATTCCTC CTTAAACCGCCTCACTAAGTGACGCTAATGATGCCTACATTGCCCCGG AGACTGGGCTGTGTAGGTGCGTTCGCCTCCAGCTTTCATCGTCCGGGT TCATGATCTAACTCGTTGTACAGATGAAGCCACGTTTCCACCTCCATG ACCAGCTTGCTGCGCTGACCTATCTAGGTCGCTGGCTTGCTATCTGCA TTGCAATTGCCATGCTGGTTGGCAGTGCATCCGCCATCTTTTTGCACT CGATGGAGTGGGCCACCCAAACGCGGGACGCCAATCATTGGCTGATAT GGGGACTCCCATTCGCAGGCTTCGATGTCGACAC | 5 |
| CGCCGCCATAAGCAGA | 6 |
| CAACACACUAUGACACGGCCCAGGCCG | 7 |
| GCCUGGGCCGUGUCAUAGUGUGUG | 8 |
| UUGUAGUCCUCACACCACUCCAACGUC | 9 |
| CGUUGGAGUGGUGUGAGGACUACAA | 10 |
| GUGUCAUGAUCUCCUAAUCCGAUAUAA | 11 |
| GUCCAAUCCAGGAGUCGGUAGAAAUA | 12 |
| GAGAGUUAAGGCAGCAUCGUGCCUCCC | 13 |

| SEQUENCE | SEQ ID NO: |
|---|---|
| GAGGCACGAUGCUGCCUUAACUCTC | 14 |
| GCCUUCGAGCACUUCAACGAGGUGCAU | 15 |
| GCACCUCGUUGAAGUGCUCGAAGGC | 16 |
| CACACCACUCCAACGUCUGCUUAUGGC | 17 |
| CAUAAGCAGACGUUGGAGUGGUGTG | 18 |
| CGGUCGAUGCAACACACUAUGACACGG | 19 |
| GUGUCAUAGUGUGUUGCAUCGACCG | 20 |

| SEQUENCE | SEQ ID NO: |
|---|---|
| CCGTCCAATTGAGGTCCGAACCGGTTTACACAAAAATTCGGAACGCCC CTGTGGGGAGGCACGATGCTGCCTTAACTCTCCGGGTGATTTCATCTT CAGCGCCGAGTGCGGATGCACCTCGTTGAAGTGCTCGAAGGCGGCGG CATCTGCAGCACTCCTTCGGCCTGGGCCGTGTCATAGTGTGTTGCATC GACCGGTTGAATCGCCGCCATAAGCAGACGTTGGAGTGGTGTGAGGA CTACAATCATTCTTTAGGAGATGGCATTCCTCCTTAAACCGCCTCACT AAGTGACGCTAATGATGCCTACATTGCCCCGGAGACTGGGCTGTGTAG GTGCGTTCGCCTCCAGCTTTCATCGTCCGGGTTCATGATCTAACTCGT TGTACAGATGAAGCCACGTTTCCACCTCCATGACCAGCTTGCTGCGCT GACCTATCTAGGTCGCTGGCTTGCTATCTGCATTGCAATTGCCATGCT GGTTGGCAGTGCATCCGCCATCTTTTTGCACTCGATGGAGTGGGCCAC CCAAACGCGGGACGCCAATCATTGGCTGATATGGGGACTCCCATTCGC AGGCTTCGATGTCGACAC | 21 |

The invention claimed is:

1. An siRNA molecule targeting nucleotides 418-444 of human HSR1 (SEQ ID NO: 5).

2. The siRNA molecule of claim 1 comprising the sequence UGGCAAUUGCAAUGCAGAUAGCAAGCC (SEQ ID NO: 3) and the sequence CUUGCUAUCUG-CAUUGCAAUUGCCA (SEQ ID NO: 4).

3. A composition comprising the siRNA molecule of claim 1 and a carrier and/or excipient.

4. A vector encoding the siRNA molecule of claim 1.

5. The composition of claim 3, which is a pharmaceutical composition comprising a pharmaceutically acceptable carrier and/or excipient.

6. The siRNA molecule of claim 2 which consists of the duplex:
   5'-rUrGrGrCrArArUrUrGrCrArArUrGrCrArGrArUrAr-GrCrArArGrCrC-3' (SEQ ID NO: 3)
   5'-rCrUrUrGrCrUrArUrCrUrGrCrArUrUrGrCrArArU-rUrGrCCA-3' (SEQ ID NO: 4).

7. The siRNA molecule of claim 1, wherein said siRNA molecule comprises a deoxyribonucleotide and/or a modification.

8. A method for inhibiting a stress response in a cell comprising administering to the cell the siRNA molecule of claim 1.

9. A method for increasing sensitivity of a cancer cell to a treatment comprising administering to the cell the siRNA molecule of claim 1.

10. A method for treating a cancer or improving efficiency of an anti-cancer treatment in a mammal in need thereof comprising administering to the mammal an effective amount of the siRNA molecule of claim 1.

\* \* \* \* \*